OTHER PUBLICATIONS

United States Patent [19]
Ivy et al.
[11] Patent Number: 6,136,561
[45] Date of Patent: Oct. 24, 2000
[54] **METHODS OF PREPARING CARBOXY-TERMINALLY TRUNCATED RECOMBINANT FLAVIVIRUS ENVELOPE G

Putnak, R.A., "Progress in the Development of Recombinant Vaccines Against Dengue and Other Arthopod–borne Flaviviruses," *Modern Vaccinology*, E. Kurstak, ed. New York: Plenum Medical, 1994, chapter 11, 231–252.

Roehrig et al., "Mapping of Biologically Active Helper T–cell Epitopes on the Flavivirus Envelope Glycoprotein," *Vaccines 92*, Cold Spring Harbor Laboratory Press, 1992, p. 277–281.

Srivastava, A.K. et al., "Immunogenicity of Peptides Cleaved by Cyanogen Bromide from Japanese Encephalitis Virus Envelope Glycoprotein E," *Acta Virol* (1990) 34:228–238.

Srivastava, A.K. et al., "Japanese Encephalitis Virus Fusion Protein with Protein A Expressed in *Escherichia coli* Confers Protective Immunity in Mice," *Microbiol Immunol* (1991) 35:863–870.

Trirawatanapong, T. et al., "Mapping of a region of dengue virus type–2 glycoprotein required for binding by a neutralizng monoclonal antibody," *Gene* (1992) 116:139–150.

Winkler, G. et al., "Characterization of a Disulphide Bridge–stabilized Antigenic Domain of Tick–borne Encephalitis Virus Structural Glycoprotein," *J. Gen Virol* (1987) 68:2239–2244.

FIG.1

```
                Capsid
                |     *
  97          ATGA ATAACCAACG GAAAAAGGCG AGAAACACGC CTTTCAATAT
 141 GCTGAAACGC GAGAGAAACC GCGTGTCAAC TGTACAACAG TTGACAAAGA
 191 GATTCTCACT TGGAATGCTG CAGGGACGAG GACCACTAAA ATTGTTCATG
 241 GCCCTGGTGG CATTCCTTCG TTTCCTAACA ATCCCACCAA CAGCAGGGAT
 291 ATTAAAAAGA TGGGGAACAA TTAAAAAATC AAAGGCTATT AATGTTCTGA
 341 GAGGCTTCAG GAAAGAGATT GGAAGGATGC TGAATATCTT AAACAGGAGA
                                                     preMembrane
                                                     |
 391 CGTAGAACTG CAGGCATGAT CATCATGCTG ATTCCAACAG TGATGGCGTT
 441 TCATCTGACC ACACGCAACG GAGAACCACA CATGATCGTC AGTAGACAAG
 491 AAAAAGGGAA AAGCCTTCTG TTTAAGACAA AGGACGGCAC GAACATGTGT
 541 ACCCTCATGG CCATGGACCT TGGTGAGTTG TGTGAAGACA CAATCACGTA
 591 TAAATGTCCC TTTCTCAAGC AGAACGAACC AGAAGACATA GATTGTTGGT
 641 GCAACTCCAC GTCCACATGG GTAACTTATG GGACATGTAC CACCACAGGA
                         Membrane
                         |
 691 GAGCACAGAA GAGAAAAAAG ATCAGTGGCG CTTGTTCCAC ACGTGGGAAT
 741 GGGATTGGAG ACACGAACTG AAACATGGAT GTCATCAGAA GGGGCCTGGA
 791 AACATGCCCA GAGAATTGAA ACTTGGATTC TGAGACATCC AGGCTTTACC
 841 ATAATGGCCG CAATCCTGGC ATACACCATA GGAACGACGC ATTTCCAAAG
                                                     Envelope
                                                     |
 891 AGTCCTGATA TTCATCCTAC TGACAGCCAT CGCTCCTTCA ATGACAATGC
 941 GCTGCATAGG AATATCAAAT AGGGACTTTG TGGAAGGAGT GTCAGGAGGG
 991 AGTTGGGTTG ACATAGTTTT AGAACATGGA AGTTGTGTGA CGACGATGGC
1041 AAAAAATAAA CCAACACTGG ACTTTGAACT GATAAAAACA GAAGCCAAAC
1091 AACCCGCCAC CTTAAGGAAG TACTGTATAG AGGCTAAACT GACCAACACG
1141 ACAACAGACT CGCGCTGCCC AACACAAGGG GAACCCACCC TGAATGAAGA
1191 GCAGGACAAA AGGTTTGTCT GCAAACATTC CATGGTAGAC AGAGGATGGG
1241 GAAATGGATG TGGATTATTT GGAAAAGGAG GCATCGTGAC CTGTGCCATG
                                     A
1291 TTCACATGCA AAAAGAACAT GGAGGGAAAA ATTGTGCAGC CAGAAAACCT
                        G
1341 GGAATACACT GTCGTTATAA CACCTCATTC AGGGGAAGAA CATGCAGTCG
1391 GAAATGACAC AGGAAAACAT GGTAAAGAAG TCAAGATAAC ACCACAGAGC
1441 TCCATCACAG AGGCGGAACT GACAGGCTAT GGCACTGTTA CGATGGAGTG
1491 CTCTCCAAGA ACGGGCCTCG ACTTCAATGA GATGGTGTTG CTGCAAATGA
1541 AAGACAAAGC TTGGCTGGTG CACAGACAAT GGTTCCTAGA CCTACCGTTG
1591 CCATGGCTGC CCGGAGCAGA CACACAAGGA TCAAATTGGA TACAGAAAGA
```

FIG.2A

```
1641 GACACTGGTC ACCTTCAAAA ATCCCCATGC GAAAAAACAG GATGTTGTTG
1691 TCTTAGGATC CCAAGAGGGG GCCATGCATA CAGCACTCAC AGGGGCTACG
1741 GAAATCCAGA TGTCATCAGG AAACCTGCTG TTCACAGGAC ATCTTAAGTG
1791 CAGGCTGAGA ATGGACAAAT ACAACTTAA AGGGATGTCA TACTCCATGT
                        A
1841 GCACAGGAAA GTTTAAAGTT GTGAAGGAAA TAGCAGAAAC ACAACATGGA
                                                          *
1891 ACAATAGTCA TTAGAGTACA ATATGAAGGA GACGGCTCTC CATGCAAGAT
1941 CCCTTTTGAG ATAATGGATC TGGAAAAAAG ACATGTTTTG GGCCGCCTGA
     *                                    T*
1991 TCACAGTCAA CCCAATTGTA ACAGAAAAGG ACAGCCCAGT CAACATAGAA
2041 GCAGAACCTC CATTCGGAGA CAGCTACATC ATCATAGGAG TGGAACCAGG
2091 ACAATTGAAG CTGGACTGGT TCAAGAAAGG AAGTTCCATC GGCCAAATGT
2141 TTGAGACAAC AATGAGGGGA GCGAAAAGAA TGGCCATTTT GGGCGACACA
2191 GCCTGGGATT TTGGATCTCT GGGAGGAGTG TTCACATCAA TAGGAAAGGC
2241 TCTCCACCAG GTTTTTGGAG CAATCTACGG GGCTGCTTTC AGTGGGGTCT
2291 CATGGACTAT GAAGATCCTC ATAGGAGTTA TCATCACATG GATAGGAATG
2341 AACTCACGTA GCACATCACT GTCTGTGTCA CTGGTATTAG TGGGAATCGT
                                                      NS1
                   N                                   |
2391 GACACTGTAC TTGGGAGTTA TGGTGCAGGC CGATAGTGGT TGCGTTGTGA
2441 GCTGGAAGAA CAAAGAACTA AAATGTGGCA GTGGAATATT CGTCACAGAT
2491 AACGTGCATA CATGGACAGA ACAATACAAG TTCCAACCAG AATCCCCTTC
2541 AAAACTGGCT TCAGCCATCC AGAAAGCTCA TGAAGAGGGC ATCTGTGGAA
2591 TCCGCTCAGT AACAAGACTG GAAAATCTTA TGTGGAAACA AATAACATCA
2641 GAATTGAATC ATATTCTATC AGAAAATGAA GTGAAACTGA CCATCATGAC
2691 AGGAGACATC AAAGGAATCA TGCAGGTAGG AAAACGATCT CTGCGGCCTC
2741 AACCCACTGA GTTGAGGTAT TCATGGAAAA CATGGGGTAA AGCGAAAATG
2791 CTCTCCACAG AACTCCATAA TCAGACCTTC CTCATTGATG GTCCCGAAAC
2841 AGCAGAATGC CCCAACACAA ACAGAGCTTG GAATTCACTA GAAGTTGAGG
2891 ACTACGGCTT TGGAGTATTC ACTACCAATA TATGGCTAAG ATTGAGAGAA
2941 AAGCAGGATG CATTTTGTGA CTCAAAACTC ATGTCAGCGG CCATAAAGGA
2991 CAACAGAGCC GTCCATGCTG ATATGGGTTA TTGGATAGAA AGCGCACTCA
3041 ATGATACATG GAAGATAGAG AAAGCTTCTT TCATTGAAGT CAAAAGTTGC
3091 CACTGGCCAA AGTCACACAC TCTATGGAGT AATGGAGTGC TAGAAAGCGA
3141 GATGGTAATT CCAAAGAATT TCGCTGGACC AGTGTCACAA CATAATAACA
3191 GACCAGGCTA TCACACACAA ACAGCAGGAC CTTGGCATCT AGGCAAGCTT
3241 GAGATGGACT TTGATTTCTG CGAAGGGACT ACAGTGGTGG TAACCGAGGA
3291 CTGTGGAAAC AGAGGGCCCT CTTTAAGAAC AACCACTGCC TCAGGAAAAC
3341 TCATAACGGA ATGGTGTTGT CGATCTTGCA CACTACCACC ACTAAGATAC
3391 AGAGGTGAGG ATGGATGCTG GTACGGGATG GAAATCAGAC CATTGAAAGA
3441 GAAAGAAGAA AATCTGGTCA GTTCTCTGGT CACAGCC
```

FIG. 2B

```
 97                                      ATGA ATAACCAACG GAAAAAGGCG AGAAACACGC
                                         Met  AsnAsnGlnArg LysLysAla  ArgAsnThr>
                                           ◆ Capsid 131 CTTTCAATAT GCTGAAACGC GAGAGAAACC GCGTGTCAAC TGTACAACAG TTGACAAAGA
    ProPheAsnMet LeuLysArg GluArgAsn ArgValSerThr ValGlnGln  LeuThrLys>

191 GATTCTCACT TGGAATGCTG CAGGGACGAG GACCACTAAA ATTGTTCATG GCCCTGGTGG
    ArgPheSerLeu GlyMetLeu GlnGlyArg  GlyProLeuLys LeuPheMet  AlaLeuVal>

251 CATTCCTTCG TTTCCTAACA ATCCCACCAA CAGCAGGGAT ATTAAAAAGA TGGGGAACAA
    AlaPheLeuArg PheLeuThr IleProPro ThrAlaGlyIle LeuLysArg  TrpGlyThr>

311 TTAAAAAATC AAAGGCTATT AATGTTCTGA GAGGCTTCAG GAAAGAGATT GGAAGGATGC
    IleLysLysSer LysAlaIle AsnValLeu ArgGlyPheArg LysGluIle  GlyArgMet>

371 TGAATATCTT AAACAGGAGA CGTAGAACTG CAGGCATGAT CATCATGCTG ATTCCAACAG
    LeuAsnIleLeu AsnArgArg ArgArgThr AlaGlyMetIle IleMetLeu  IleProThr>

431 TGATGGCGTT TCATCTGACC ACACGCAACG GAGAACCACA CATGATCGTC AGTAGACAAG
    ValMetAlaPhe HisLeuThr ThrArgAsn GlyGluProHis MetIleVal  SerArgGln>
          ◆ PreMembrane 491 AAAAAGGGAA AAGCCTTCTG TTTAAGACAA AGGACGGCAC GAACATGTGT ACCCTCATGG
    GluLysGlyLys SerLeuLeu PheLysThr LysAspGlyThr AsnMetCys  ThrLeuMet>

551 CCATGGACCT TGGTGAGTTG TGTGAAGACA CAATCACGTA TAAATGTCCC TTTCTCAAGC
    AlaMetAspLeu GlyGluLeu CysGluAsp ThrIleThrTyr LysCysPro  PheLeuLys>

611 AGAACGAACC AGAAGACATA GATTGTTGGT GCAACTCCAC GTCCACATGG GTAACTTATG
    GlnAsnGluPro GluAspIle AspCysTrp CysAsnSerThr SerThrTrp  ValThrTyr>

671 GGACATGTAC CACCACAGGA GAGCACAGAA GAGAAAAAAG ATCAGTGGCG CTTGTTCCAC
    GlyThrCysThr ThrThrGly GluHisArg ArgGluLysArg SerValAla  LeuValPro>
                                                       ◆ Membrane 731 ACGTGGGAAT GGGATTGGAG ACACGAACTG AAACATGGAT GTCATCAGAA GGGGCCTGGA
    HisValGlyMet GlyLeuGlu ThrArgThr GluThrTrpMet SerSerGlu  GlyAlaTrp>

791 AACATGCCCA GAGAATTGAA ACTTGGATTC TGAGACATCC AGGCTTTACC ATAATGGCCG
    LysHisAlaGln ArgIleGlu ThrTrpIle LeuArgHisPro GlyPheThr  IleMetAla>
```

FIG.3A

851 CAATCCTGGC ATACACCATA GGAACGACGC ATTTCCAAAG AGTCCTGATA TTCATCCTAC
AlaIleLeuAla TyrThrIle GlyThrThr HisPheGlnArg ValLeuIle PheIleLeu>

911 TGACAGCCAT CGCTCCTTCA ATGACAATGC GCTGCATAGG AATATCAAAT AGGGACTTTG
LeuThrAlaIle AlaProSer MetThrMet ArgCysIleGly IleSerAsn ArgAspPhe>
◆ Envelope 971 TGGAAGGAGT GTCAGGAGGG AGTTGGGTTG ACATAGTTTT AGAACATGGA AGTTGTGTGA
ValGluGlyVal SerGlyGly SerTrpVal AspIleValLeu GluHisGly SerCysVal>

1031 CGACGATGGC AAAAAATAAA CCAACACTGG ACTTTGAACT GATAAAAACA GAAGCCAAAC
ThrThrMetAla LysAsnLys ProThrLeu AspPheGluLeu IleLysThr GluAlaLys>

1091 AACCCGCCAC CTTAAGGAAG TACTGTATAG AGGCTAAACT GACCAACACG ACAACAGACT
GlnProAlaThr LeuArgLys TyrCysIle GluAlaLysLeu ThrAsnThr ThrThrAsp>

1151 CGCGCTGCCC AACACAAGGG GAACCCACCC TGAATGAAGA GCAGGACAAA AGGTTTGTCT
SerArgCysPro ThrGlnGly GluProThr LeuAsnGluGlu GlnAspLys ArgPheVal>

1211 GCAAACATTC CATGGTAGAC AGAGGATGGG GAAATGGATG TGGATTATTT GGAAAAGGAG
CysLysHisSer MetValAsp ArgGlyTrp GlyAsnGlyCys GlyLeuPhe GlyLysGly>

WT                                                            GAA(Glu)
1271 GCATCGTGAC CTGTGCCATG TTCACATGCA AAAAGAACAT GGAGGGAAAA ATTGTGCAGC
GlyIleValThr CysAlaMet PheThrCys LysLysAsnMet GluGlyLys IleValGln>

WT                              GTG(Val)
1331 CAGAAAACCT GGAATACACT GTCGTTATAA CACCTCATTC AGGGGAAGAA CATGCAGTCG
ProGluAsnLeu GluTyrThr ValValIle ThrProHisSer GlyGluGlu HisAlaVal>

1391 GAAATGACAC AGGAAAACAT GGTAAAGAAG TCAAGATAAC ACCACAGAGC TCCATCACAG
GlyAsnAspThr GlyLysHis GlyLysGlu ValLysIleThr ProGlnSer SerIleThr>

1451 AGGCGGAACT GACAGGCTAT GGCACTGTTA CGATGGAGTG CTCTCCAAGA ACGGGCCTCG
GluAlaGluLeu ThrGlyTyr GlyThrVal ThrMetGluCys SerProArg ThrGlyLeu>

1511 ACTTCAATGA GATGGTGTTG CTGCAAATGA AAGACAAAGC TTGGCTGGTG CACAGACAAT
AspPheAsnGlu MetValLeu LeuGlnMet LysAspLysAla TrpLeuVal HisArgGln>

1571 GGTTCCTAGA CCTACCGTTG CCATGGCTGC CCGGAGCAGA CACACAAGGA TCAAATTGGA
TrpPheLeuAsp LeuProLeu ProTrpLeu ProGlyAlaAsp ThrGlnGly SerAsnTrp>

FIG.3B

```
1631 TACAGAAAGA GACACTGGTC ACCTTCAAAA ATCCCCATGC GAAAAAACAG GATGTTGTTG
     IleGlnLysGlu ThrLeuVal ThrPheLys AsnProHisAla LysLysGln AspValVal>

1691 TCTTAGGATC CCAAGAGGGG GCCATGCATA CAGCACTCAC AGGGGCTACG GAAATCCAGA
     ValLeuGlySer GlnGluGly AlaMetHis ThrAlaLeuThr GlyAlaThr GluIleGln>

1751 TGTCATCAGG AAACCTGCTG TTCACAGGAC ATCTTAAGTG CAGGCTGAGA ATGGACAAAT
     MetSerSerGly AsnLeuLeu PheThrGly HisLeuLysCys ArgLeuArg MetAspLys>

WT                                                    ATT(Ile)
1811 TACAACTTAA AGGGATGTCA TACTCCATGT GCACAGGAAA GTTTAAAGTT GTGAAGGAAA
     LeuGlnLeuLys GlyMetSer TyrSerMet CysThrGlyLys PheLysVal ValLysGlu>

1871 TAGCAGAAAC ACAACATGGA ACAATAGTCA TTAGAGTACA AIATGAAGGA GACGGCTCTC
     IleAlaGluThr GlnHisGly ThrIleVal IleArgValGln TyrGluGly AspGlySer>

1931 CATGCAAGAT CCCTTTTGAG ATAATGGATC TGGAAAAAAG ACATGTTTTG GGCCGCCTGA
     ProCysLysIle ProPheGlu IleMetAsp LeuGluLysArg HisValLeu GlyArgLeu>

WT                                       AGT(Ser)
1991 TCACAGTCAA CCCAATTGTA ACAGAAAAGG ACAGCCCAGT CAACATAGAA GCAGAACCTC
     IleThrValAsn ProIleVal ThrGluLys AspSerProVal AsnIleGlu AlaGluPro>

2051 CATTCGGAGA CAGCTACATC ATCATAGGAG TGGAACCAGG ACAATTGAAG CTGGACTGGT
     ProPheGlyAsp SerTyrIle IleIleGly ValGluProGly GlnLeuLys LeuAspTrp>

2111 TCAAGAAAGG AAGTTCCATC GGCCAAATGT TTGAGACAAC AATGAGGGGA GCGAAAAGAA
     PheLysLysGly SerSerIle GlyGlnMet PheGluThrThr MetArgGly AlaLysArg>

2171 TGGCCATTTT GGGCGACACA GCCTGGGATT TTGGATCTCT GGGAGGAGTG TTCACATCAA
     MetAlaIleLeu GlyAspThr AlaTrpAsp PheGlySerLeu GlyGlyVal PheThrSer>

2231 TAGGAAAGGC TCTCCACCAG GTTTTTGGAG CAATCTACGG GGCTGCTTTC AGTGGGGTCT
     IleGlyLysAla LeuHisGln ValPheGly AlaIleTyrGly AlaAlaPhe SerGlyVal>

2291 CATGGACTAT GAAGATCCTC ATAGGAGTTA TCATCACATG GATAGGAATG AACTCACGTA
     SerTrpThrMet LysIleLeu IleGlyVal IleIleThrTrp IleGlyMet AsnSerArg>

2351 GCACATCACT GTCTGTGTCA CTGGTATTAG TGGGAATCGT GACACTGTAC TTGGGAGTTA
     SerThrSerLeu SerValSer LeuValLeu ValGlyIleVal ThrLeuTyr LeuGlyVal>
```

FIG.3C

2411 TGGTGCAGGC CGATAGTGGT TGCGTTGTGA GCTGGAAGAA CAAAGAACTA AAATGTGGCA
     MetValGlnAla AspSerGly CysValVal SerTrpLysAsn LysGluLeu LysCysGly>
        ◆ NS1

2471 GTGGAATATT CGTCACAGAT AACGTGCATA CATGGACAGA ACAATACAAG TTCCAACCAG
     SerGlyIlePhe ValThrAsp AsnValHis ThrTrpThrGlu GlnTyrLys PheGlnPro>

2531 AATCCCCTTC AAAACTGGCT TCAGCCATCC AGAAAGCTCA TGAAGAGGGC ATCTGTGGAA
     GluSerProSer LysLeuAla SerAlaIle GlnLysAlaHis GluGluGly IleCysGly>

2591 TCCGCTCAGT AACAAGACTG GAAAATCTTA TGTGGAAACA AATAACATCA GAATTGAATC
     IleArgSerVal ThrArgLeu GluAsnLeu MetTrpLysGln IleThrSer GluLeuAsn>

2651 ATATTCTATC AGAAAATGAA GTGAAACTGA CCATCATGAC AGGAGACATC AAAGGAATCA
     HisIleLeuSer GluAsnGlu ValLysLeu ThrIleMetThr GlyAspIle LysGlyIle>

2711 TGCAGGTAGG AAAACGATCT CTGCGGCCTC AACCCACTGA GTTGAGGTAT TCATGGAAAA
     MetGlnValGly LysArgSer LeuArgPro GlnProThrGlu LeuArgTyr SerTrpLys>

2771 CATGGGGTAA AGCGAAAATG CTCTCCACAG AACTCCATAA TCAGACCTTC CTCATTGATG
     ThrTrpGlyLys AlaLysMet LeuSerThr GluLeuHisAsn GlnThrPhe LeuIleAsp>

2831 GTCCCGAAAC AGCAGAATGC CCCAACACAA ACAGAGCTTG GAATTCACTA GAAGTTGAGG
     GlyProGluThr AlaGluCys ProAsnThr AsnArgAlaTrp AsnSerLeu GluValGlu>

2891 ACTACGGCTT TGGAGTATTC ACTACCAATA TATGGCTAAG ATTGAGAGAA AAGCAGGATG
     AspTyrGlyPhe GlyValPhe ThrThrAsn IleTrpLeuArg LeuArgGlu LysGlnAsp>

2951 CATTTTGTGA CTCAAAACTC ATGTCAGCGG CCATAAAGGA CAACAGAGCC GTCCATGCTG
     AlaPheCysAsp SerLysLeu MetSerAla AlaIleLysAsp AsnArgAla ValHisAla>

3011 ATATGGGTTA TTGGATAGAA AGCGCACTCA ATGATACATG GAAGATAGAG AAAGCTTCTT
     AspMetGlyTyr TrpIleGlu SerAlaLeu AsnAspThrTrp LysIleGlu LysAlaSer>

3071 TCATTGAAGT CAAAAGTTGC CACTGGCCAA AGTCACACAC TCTATGGAGT AATGGAGTGC
     PheIleGluVal LysSerCys HisTrpPro LysSerHisThr LeuTrpSer AsnGlyVal>

3131 TAGAAAGCGA GATGGTAATT CCAAAGAATT TCGCTGGACC AGTGTCACAA CATAATAACA
     LeuGluSerGlu MetValIle ProLysAsn PheAlaGlyPro ValSerGln HisAsnAsn>

3191 GACCAGGCTA TCACACACAA ACAGCAGGAC CTTGGCATCT AGGCAAGCTT GAGATGGACT
     ArgProGlyTyr HisThrGln ThrAlaGly ProTrpHisLeu GlyLysLeu GluMetAsp>

FIG.3D

3251 TTGATTTCTG CGAAGGGACT ACAGTGGTGG TAACCGAGGA CTGTGGAAAC AGAGGGCCCT
     PheAspPheCys GluGlyThr ThrValVal ValThrGluAsp CysGlyAsn ArgGlyPro>

3311 CTTTAAGAAC AACCACTGCC TCAGGAAAAC TCATAACGGA ATGGTGTTGT CGATCTTGCA
     SerLeuArgThr ThrThrAla SerGlyLys LeuIleThrGlu TrpCysCys ArgSerCys>

3371 CACTACCACC ACTAAGATAC AGAGGTGAGG ATGGATGCTG GTACGGGATG GAAATCAGAC
     ThrLeuProPro LeuArgTyr ArgGlyGlu AspGlyCysTrp TyrGlyMet GluIleArg>

3431 CATTGAAAGA GAAAGAAGAA AATCTGGTCA GTTCTCTGGT CACAGCC
     ProLeuLysGlu LysGluGlu AsnLeuVal SerSerLeuVal ThrAla

FIG.3E

Before mutagenesis:
```
1789                        Trypsin                            1848
 |                            ↓                                  |
5'-TGCAGGCTGAGAATGGACAAATTACAACTTAAAGGGATGTCATACTCCATGTGCACAGGA-3'
   CysArgLeuArgMetAspLysLeuGlnLeuLysGlyMetSerTyrSerMetCysThrGly
```

Mutagenizing Oligonucleotide:
```
    3'-CCGACTCTTACCTGTTTA              CCCTACAGTATGAGG-5'
                         ╲             |
                          ctatcagctgtcga
```

After mutagenesis:        SalI    PvuII
```
                            v       v
5'-TGCAGGCTGAGAATGGACAAATgatagtcgacagctGGGATGTCATACTCCATGTGCACAGGA-3'
...CysArgLeuArgMetAspLysEndEnd        GlyMetSerTyrSerMetCysThrGly...
      C-terminus of 60%E              N-terminus of domain B
```

FIG.4

5318 ATGAGATTTCCTTCAATTTTTACTGCAGTTTTATTCGCAGCATCCTCCGC
     MetArgPheProSerIlePheThrAlaValLeuPheAlaAlaSerSerAla>
     ↦ MFα secretion signal peptide 5368 ATTAGCTGCTCCAGTCAACACTACAACAGAAGATGAAACGGCACAAATTC
     LeuAlaAlaProValAsnThrThrThrGluAspGluThrAlaGlnIle>
     ▲ Signalase cleavage
     ↦ MFα propeptide 5418 CGGCTGAAGCTGTCATCGGTTACTCAGATTTAGAAGGGGATTTCGATGTT
     ProAlaGluAlaValIleGlyTyrSerAspLeuGluGlyAspPheAspVal>

5468 GCTGTTTTGCCATTTTCCAACAGCACAAATAACGGGTTATTGTTTATAAA
     AlaValLeuProPheSerAsnSerThrAsnAsnGlyLeuLeuPheIleAsn>

5518 TACTACTATTGCCAGCATTGCTGCTAAAGAAGAAGGGGTATCTCTCGAGA
     ThrThrIleAlaSerIleAlaAlaLysGlnGluGlyValSerLeuGlu>

5568 AAAGGGAGGCTGGGATGTCATACTCCATGTGCACAGGAAAGTTTAAAGTT
     LysArgGluAlaGlyMetSerTyrSerMetCysThrGlyLysPheLysVal>
     ▲ Kex2p cleavage
     ↦ Domain B 5618 GTGAAGGAAATAGCAGAAACACAACATGGAACAATAGTCATTAGAGTACA
     ValLysGluIleAlaGluThrGlnHisGlyThrIleValIleArgValGln>

5668 ATATGAAGGAGACGGCTCTCCATGCAAGATCCCTTTTGAGATAATGGATC
     TyrGluGlyAspGlySerProCysLysIleProPheGluIleMetAsp>

5718 TGGAAAAAAGACATGTTTTGGGCCGCCTGATCACAGTCAATCCAATTGTA
     LeuGluLysArgHisValLeuGlyArgLeuIleThrValAsnProIleVal>

5768 ACAGAAAAGGACAGCCCAGTCAACATAGAAGCAGAACCTCCATTCGGAGA
     ThrGluLysAspSerProValAsnIleGluAlaGluProProPheGlyAsp>

5818 CAGCTACATCATCATAGGAGTGGAACCAGGACAATTGAAGCTGGACTGGT
     SerTyrIleIleIleGlyValGluProGlyGlnLeuLysLeuAspTrp>

5868 TCAAGAAAGGATAA
     PheLysLysGlyEnd>

FIG.7

```
          220         230         240         250         260         270         280
           *           *           *           *           *           *           *
    GACGGCTCTC CATGCAAGAT CCCTTTTGAG ATAATGGATC TGGAAAAAAG ACATGTTTG  GGCCGCCTGA
    CTGCCGAGAG GTACGTTCTA GGGAAAACTC TATTACCTAG ACCTTTTTC  TGTACAAAAC CCGGCGGACT
    AspGlySer ProCysLysIle ProPheGlu IleMetAsp LeuGluLysArg HisValLeu GlyArgLeu>
                        C                             RGARSP-Domain B         C             C                ^

290         300         310         320         330         340         350
           *           *           *           *           *           *           *
    TCACAGTCAA CCCAATTGTA ACAGAAAAGG ACAGTCCAGT CAACATAGAA GCAGAACCTC CATTCGGAGA
    AGTGTCAGTT GGGTTAACAT TGTCTTTTCC TGTCAGGTCA GTTGTATCTT CGTCTTGGAG GTAAGCCTCT
    IleThrValAsn ProIleVal ThrGluLys AspSerProVal AsnIleGlu AlaGluPro ProPheGlyAsp>
                        C                             RGARSP-Domain B         C             C                ^

360         370         380         390         400         410
           *           *           *           *           *           *
    CAGCTACATC ATCATAGGAG TGGAACCAGG ACAATTGAAG CTGGACTGGT TCAAGAAAGG ATAATAG
    GTCGATGTAG TAGTATCCTC ACCTTGGTCC TGTTAACTTC GACCTGACCA AGTTCTTTCC TATTATC
    SerTyrIle IleIleGly ValGluProGly GlnLeuLys LeuAspTrp PheLysLysGly EndEnd>
                        C                             RGARSP-Domain B_C        C                ^
```

FIG.9B

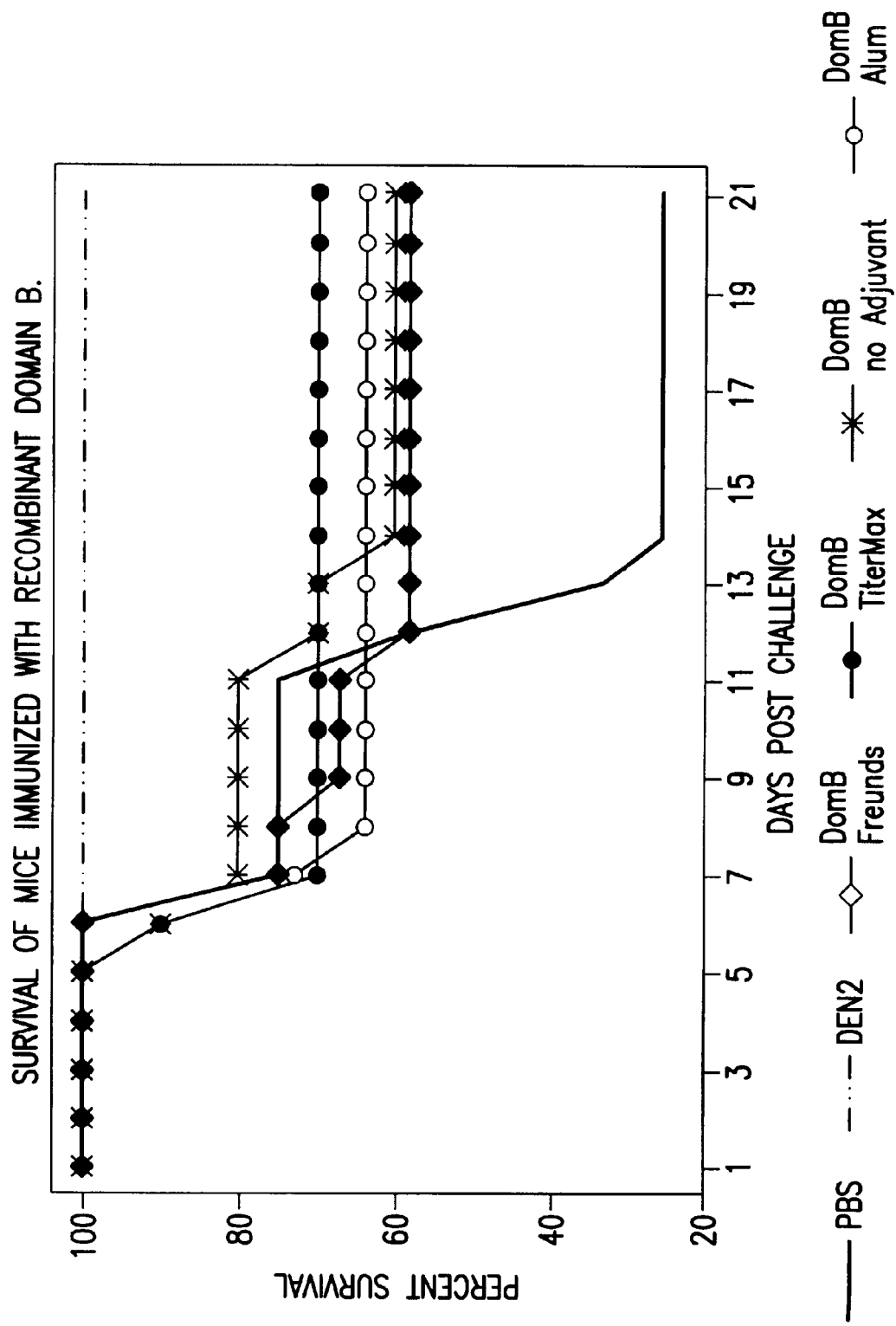

CONSTRUCTION OF THE pMttDomB EXPRESSION PLASMID

METHODS OF PREPARING CARBOXY-TERMINALLY TRUNCATED RECOMBINANT FLAVIVIRUS ENVELOPE GLYCOPROTEINS EMPLOYING DROSOPHILA MELANOGASTER EXPRESSION SYSTEMS

This application is a continuation of application Ser. No. 08/488,807, filed Jun. 8, 1995, which is a continuation-in-part of application Ser. No. 08/488,734 filed May 24, 1995.

TECHNICAL FIELD

The invention relates to protection against and diagnosis of dengue fever. More specifically, the invention concerns a subunit of the dengue virus envelope protein secreted as a mature recombinantly produced protein from eucaryotic cells which is protective against dengue infection, which raises antibodies useful in passive immunization, and which is useful in diagnosis of infection by the virus.

BACKGROUND ART

The dengue viruses are members of the family Flaviviridae which also includes the Japanese encephalitis (JE) virus, Tick-borne encephalitis (TBE) virus, and the is initially discovered prototype of this class, the yellow fever (YF) virus. The flaviviruses contain a single positive strand genomic RNA and are small enveloped viruses affecting animals, but generally transmitted to vertebrates by chronically infected mosquito or tick vectors. Flaviviruses are enveloped by host cell membrane and contain the three structural proteins capsid (C), membrane (M), and envelope (E). The E and M proteins are found on the surface of the virion where they are anchored in the membrane. Mature E is glycosylated, whereas M is not, although its precursor, preM, is a glycoprotein. Glycoprotein E, the largest structural protein, contains functional domains responsible for cell surface attachment and intraendosomal fusion activities. It is also a major target of the host immune system, inducing neutralizing antibodies, protective immunity, as well as antibodies which inhibit hemagglutination.

Dengue virus is the causative agent of dengue fever and is transmitted to man by Aedes mosquitoes, principally *Aedes aegypti* and *Aedes albopictus*. Classic dengue fever is an acute illness marked by fever, headache, aching muscles and joints, and rash. A fraction of cases, typically in children, results in more extreme forms of infection, i.e., dengue hemorrhagic fever (DHF) or dengue shock syndrome (DSS). Without diagnosis and prompt medical intervention, the sudden onset and rapid progress of DHF/DSS can be fatal.

Dengue is one of the most important virus groups transmitted to man by arthropods in terms of global morbidity; it has been estimated that dengue is responsible for up to 100 million illnesses annually. With the advent of modern jet travel, dengue has spread globally in the tropics and subtropics, and multiple dengue serotypes in a region are common.

Every flavivirus genome is a single positive-stranded RNA of approximately 10,500 nucleotides containing short 5' and 3' untranslated regions, a single long open reading frame (ORF), a 5' cap, and a nonpolyadenylated 3' terminus. The ten gene products encoded by the single, long open reading frame are contained in a polyprotein organized in the order, C (capsid), preM/M (membrane), E (envelope), NS1 (nonstructural), NS2a, NS2b, NS3, NS4a, NS4b, and NS5 (Chambers, T. J. et al. *Ann Rev Microbiol* (1990) 44:649–688). Processing of the encoded polyprotein is initiated cotranslationally, and full maturation requires both host and viral-specific proteases. The sites of proteolytic cleavage in the YF virus have been determined by comparing the nucleotide sequence and the amino terminal sequences of the viral proteins. Subsequent to initial processing of the polyprotein, preM is converted to M during virus release (Wengler, G. et al. *J Virol* (1989) 63:2521–2526), and anchored C is processed during virus maturation (Nowak et al. *Virology* (1987) 156:127–137).

There are four antigenically related dengue viruses which, however, can be recognized as distinct serotypes. The complete genomic sequence for at least one strain of each of the four dengue serotypes has been reported (DEN-1, Fu, J. et al. *Virology* (1992) 188:953–958; DEN-2, Deubel, V. et al. *Virology* (1986) 155:365–377; Hahn, Y. S. et al. *Virology* (1988) 162:167–180; DEN-3, Osatomi, K. et al. *Virus Genes* (1988) 2:99–108; Osatomi, K. et al. *Virology* (1990) 176:643–647; DEN-4, Zhao, B. E. et al. *Virology* (1986) 155:77–88; Mackow, E. et al. *Virology* (1987) 159:217–228). In addition, the compete genomic sequences of other flaviviruses are known (e.g., YF virus: Rice et al., *Science* (1985) 229:726–733).

It does not appear that infection by one dengue serotype can confer long-term immunity on the individual with respect to other serotypes. In fact, secondary infections with heterologous serotypes are quite common. In general, antibody responses in infected subjects to primary infection are mostly IgM antibodies and these antibodies are directed against type-specific determinants. On the other hand, secondary infections by heterologous serotypes generate IgG antibodies which are flavivirus crossreactive.

Helpful reviews of the nature of the dengue disease, the history of attempts to develop suitable vaccines, and structural features of flaviviruses in general as well as the molecular structural features of the envelope protein of flaviviruses are found in Halstead, S. B. *Science* (1988) 239:476–481; Brandt, W. E. *J Infect Disease* (1990) 162:577–583; Chambers, T. J. et al. *Annual Rev Microbiol* (1990) 44:649–688; Mandl, C. W. et al. *Virology* (1989) 63:564–571; and Henchal, E. A. and J. R. Putnak, *Clin Microbiol Rev* (1990) 3:376–396.

A successful vaccine for protection against dengue infection has never been developed. However, there have been a number of preliminary efforts, many of which focus on the envelope protein, since this protein is exposed at the surface and is believed to be responsible for eliciting immunity.

Monoclonal antibodies (Mabs) directed against purified E of several flaviviruses DEN-2 (Henchal et al. *Am J Trop Med Hyg* (1985) 34:162–169, TBE (Heinz, F. X. et al. *Virology* (1983) 126:525–537), St. Louis encephalitis (SLE, Mathews, J. H. et al. *J Immunol* (1984) 132:1533–1537), Murray Valley encephalitis (MVE, Hawkes, R. A. et al. *J Gen Virol* (1988) 69:1105–1109), and JE (Takegami, T. et al. *Acta Virologica* (1982) 26:312–320) are neutralizing in vitro. Some of these Mabs can also passively confer protection in vivo (Heinz, F. X. et al. (1983, supra)); Mathews, J. H. et al. (1984, supra)); Kimuro-Kuroda and Yasui, *J Immunol* (1988) 141:3603–3610).

Although the primary amino acid sequence of the flavivirus E glycoprotein is variable (45–80% identity), all have twelve conserved cysteine residues, forming six disulfide bridges, and hydrophilicity profiles are nearly superimposable, suggesting that they may all have similar secondary and tertiary structures. Based on the position of the 12 conserved cysteines (determined for West Nile virus, Nowak and Wengler, *Virology* (1987) 156:127–137), monoclonal antibody competitive binding studies, monoclonal antibody binding to purified proteolytic fragments, and analysis of neutralizing antibody escape mutants of Tick-Borne Encephalitis Virus, glycoprotein E was divided into three antigenic domains (A, B, and C) and two transmembrane segments at its carboxy-terminus. See, for example, Mandl, C. W. et al. *J Virol* (1989) 63:564–571. FIG. 1, reproduced from this article, shows the locations of these domains.

Domain A was defined as a denaturation sensitive, highly folded, and disulfide stabilized discontinuous domain composed of the amino acids from 50–125 and 200–250 containing five of the six disulfide bridges. Neutralization and hemagglutination inhibition epitopes are found within domain A, and, for dengue viruses, one of the two N-linked glycosylation sites. A conserved hydrophobic amino acid sequence within domain A has been postulated to provide fusogenic properties after low pH treatment. Amino acid sequences conserved among the flavivirus family are located within this region; thus, broadly flavivirus-cross-reactive epitopes lie within this domain.

Domain B was identified as a continuous domain composed of amino acids 301–395 (an approximate region between amino acids 300–400 for all flaviviruses). The domain can be isolated as a single immunoreactive proteolytic fragment. It has been postulated that this domain forms part of the receptor binding site (Heinz, F. X. et al. *APMIS* (1993) 101:735–745), and attenuating mutations have been mapped to sequences within domain B Heinz et al. (supra). A variety of neutralizing antibodies have been shown to specifically map to Domain B (Heinz et al. (1983, supra)); Trirawatanapong et al., 1992; Megret et al., 1992; Lin et al., 1994). The binding of these neutralizing monoclonal antibodies is dependent on formation of a disulfide bond, and in some cases also is sensitive to detergent denaturation. Species-specific monoclonal antibodies bind this domain.

Domain C represents a hypervariable loop between the two segments of Domain A. Its antigenicity is insensitive to denaturation or reducing agents, and contains one N-linked glycosylation site. Predominantly sub-type specific monoclonal antibodies react with this domain. No specific activity has been assigned to this domain.

Many strategies are currently under investigation to develop an effective and safe dengue vaccine; however, to date, no single strategy has proven completely satisfactory. Attempts to generate live attenuated dengue vaccine strains have not been entirely successful, although research into this area continues. In the absence of effective, live attenuated dengue vaccines, a significant effort has been invested in the development of recombinant, dengue subunit or viral-vectored vaccines.

Recombinant dengue proteins have been expressed in several systems to date (see Putnak, R. A. (1994) *Modern Vaccinology*, E. Kurstak ed., Plenum Medical, New York, pp. 231–252, for review). Most efforts using *Escherichia coli* have yielded poor immunogen unable to elicit neutralizing antibodies. This may reflect non-native conformation of dengue proteins expressed in the bacteria and the necessity to process the viral proteins through the secretion pathway in order to form the proper disulfide bonds, glycosylate the proteins, or both.

Several reports have described vaccinia-flavivirus recombinants expressing envelope protein as part of a polyprotein (e.g. C-preM-E-NS1; [Dengue] Zhao, B. G. et al. *J Virol* (1987) 61:4019–4022; Deubel, V. et al. *J Gen Virol* (1988) 69:1921–1929; Bray, M. et al. *J Virol* (1991) 63:2853–2856; [YF] Hahn, Y. S. et al. *Arch Virol* (1990) 115:251–265), as a single protein (e.g. 100% E; [Dengue] Bray, M. et al., *J Virol* (1989) 63:2853–2856), or as polypeptides (e.g. 79% E-RKG; Men, R. et al. *J Virol* (1991) 65:1400–1407). The most successful recombinant vaccinia viruses, those capable of inducing neutralizing antibodies and protecting mice from virus challenge, were the which were secreted E extracellularly or accumulated E on the cell surface.

Men, R. et al. (1991, supra) described the recombinant production of various C-terminal truncations of the DEN-4 envelope protein using a recombinant Vaccinia virus vector and infecting mammalian CV1 cells. The results showed that the recombinants that contain greater than 79% of the coding sequence produced an intracellular protein that could be immunoprecipitated with anti-dengue virus antibodies contained in hyperimmune mouse ascitic fluid (HMAF). Although there was a reduced level of detection for protein which contained 79% of envelope or less, this did not appear to result from reduced production of the protein. It was also found that only truncations which contained 79% of E or less were secreted efficiently; E polypeptides equal to or larger than 81% E were not secreted efficiently.

Men et al. (1991, supra) constructed additional C-terminal truncations between 79% E and 81% E to map the amino acids responsible for the difference in secretion and immunoreactivity with HMAF of these two truncated E polypeptides. The results demonstrated that 79% E containing the additional tripeptide sequence RKG was also secreted. Although both 59% E and 79% E-RKG were secreted, only 79% E-RKG was detected at the cells' surface. The recombinant Vaccinia viruses containing various truncations were also used to immunize mice. Mice immunized with recombinants expressing 79% E-RKG or larger portions of the envelope protein were protected. However, except for 59% E, mice immunized with 79% E or a smaller product were only partially protected. The 59% E elicited high protection rates (>90%) comparable to 79% E-RKG and larger C-terminal truncated E polypeptides. Protection correlated with binding to HMAF.

Combinations of immunogenic structural and nonstructural JE virus, DEN-1, DEN-2, and DEN-4 proteins have been expressed by baculovirus recombinants (Matsuura, Y. et al. *Virology* (1989) 173:674–682; Putnak, R. A. et al. *Am J Trop Med Hyg* (1991) 45:159–167; Deubel, V. et al. *Virology* (1991) 180:442–447). Baculovirus-expressed dengue and JE E glycoprotein elicited neutralizing antibodies, protected mice from a lethal dengue virus challenge, or both. In spite of these successes, the expression levels reported in baculovirus are low and the recombinant protein is less immunogenic than the viral protein (Putnak, R. A. et al. *Am J Trop Med Hyg* (1991) supra).

Research with purified polypeptides released by proteolysis of flavivirus envelope proteins, with recombinant polypeptides, and with synthetic peptides has indicated where protective epitopes may map. The isolated 9000 dalton domain B trypsin fragment from TBE virus spontaneously refolds and is stabilized by disulfide bridges (Winkler, G. et al. *J Gen Virol* (1987) 68:2239–2244). This disulfide stabilized fragment elicited neutralizing antibodies in mice (Heinz, F. X. et al. *Virology* (1984) 130:485–501). In contrast, a 28,000 dalton trypsin fragment from WN virus containing domain B sequences was unable to spontaneously refold and did not elicit neutralizing antibodies (Wengler and Wengler, 1989).

A cyanogen bromide-cleaved 8 kD fragment (amino acids 375–456) overlapping domain B from JE envelope protein was found to induce neutralizing antibodies in mice (Srivastava, A. K. et al. *Acta Virol* (1990) 34:228–238). Immunization of mice with a larger polypeptide (JE E amino acid 319 to NS1 amino acid 65) spanning the 8 kD peptide expressed in *Escherichia coli* as a fusion to protein A elicited neutralizing antibodies and protected mice from lethal virus challenge (Srivastava, A. K. et al. *Microbiol Immunol* (1991) 35:863–870). This polypeptide begins between the two cysteines within domain B, and, therefore, cannot form the stabilizing disulfide bond that earlier reports suggest is necessary for presentation of protective epitopes.

Immunization of mice with synthetic peptides corresponding to amino acids within domain B, aa 356–376 from MVE (Roehrig, J. T. et al. *Virology* (1989) 171:49–60) or aa 352–368 from DEN-2 virus (Roehrig, J. T. et al. *Virology* (1990) 177:668–675), elicited low levels of neutralizing antibodies in mice, suggesting the presence in domain B of a weak linear neutralizing epitope (Roehrig, J. T. et al. 1989 and 1990, supra).

Mason, P. W. et al. *J Gen Virol* (1990) 71:2107–2114 identified two domains of the DEN-1 envelope protein: domain I which includes amino acids 76–93 of the E protein and domain II (equivalent to domain B) which includes amino acids 293–402. These domains were identified from deletion analysis using recombinant fusion proteins expressed in *E. coli* and reacted with antiviral monoclonal antibodies. Recombinant fusion proteins containing *E. coli* trpE sequences fused to the envelope protein (amino acids 1 to 412) elicited antibodies in mice which reacted with a portion of the protein containing domain II.

In addition, Mason, P. W. et al. (*J Gen Virol* (1989) 70:2037–2049) expressed a collection of *E. coli* trpE fusion proteins to segments of JE virus envelope protein spanning domain B. The trpE fusion proteins containing the smallest JE E fragments that retained immunoreactivity with a panel of neutralizing monoclonal antibodies included amino -acid residues from methionine 303 through tryptophan 396. However, animals immunized with immunoreactive trpE fusion polypeptides did not produce neutralizing antibodies nor were they protected from lethal challenge.

Trirawatanapong, T. et al. *Gene* (1992) 116:139–150. prepared several truncated forms of dengue 2 envelope proteins in *E. coli* for epitope mapping, and mapped monoclonal antibody 3H5 to its corresponding epitope. This was first localized between amino acids 255 and 422. Targeted gene deletions in the plasmid constructs encoding the truncated proteins permitted mapping of the binding site to the 12 amino acids between positions 386 and 397. The mapping was apparently confirmed by the ability of a synthetic peptide containing E protein amino acids 386–397 to bind 3H5 specifically.

Megret, F. et 41. *Virology* (1992) 187:480–491 prepared 16 overlapping fragments of DEN-2 envelope protein as trpE fusion products in *E. coli* for epitope mapping. The fusion proteins are produced intracellularly and obtained from the lysates. These products were used to map epitopes defined by a panel of 20 monoclonal antibodies. Six antigenic domains were described: non-neutralizing antibodies bound to peptides containing amino acids 22–58, amino acids 304–332, amino acids 60–97, and amino acids 298–397. Neutralizing antibodies bound to peptides containing amino acids 60–135, 60–205, and 298–397.

Significantly, Megret et al. (1992, supra) demonstrated that all MAbs (including 3H5), with two exceptions (below), that recognize "full-length" domain B (amino acids 298–397) are unable to recognize slightly shorter polypeptides. For example, in contrast to the findings of Trirawatanapong et al. *Gene* (1992, supra), MAb 3H5 was unable to bind to trpE fusion proteins containing DEN-2 E amino acids 304–397, 298–385, or 366–424. The two exceptional MAbs in the findings of Megret et al. are MAbs 5A2 and 9D12. The pattern of binding of MAb 5A2 suggests that it recognizes a linear epitope between amino acids 304 to 332, while MAb 9D12 binds to a polypeptide, amino acids 298–385, which is slightly shorter than the smallest polypeptide (amino acids 298–397) to which MAb 3H5 binds. These results indicate that both the disulfide bond in domain B and the domain B C-terminal amino acids are involved in forming the immunodominant domain B epitopes.

Although it appears established from the art that the B domain of the flavivirus envelope protein contains epitopes which bind neutralizing antibodies, problems have arisen with respect to producing recombinant polypeptides containing the B domain in a form which mimics the native protein and is thus capable of eliciting an immune response. The only recombinantly produced E polypeptides containing the B domain that elicited a protective immune response in mice were expressed from Vaccinia and baculovirus vectors. Generally, recombinantly produced proteins lack the appropriate 100–120 amino acid peptides, wherein the extensions do not interfere with the immunogenic effectiveness or secretion of the B domain. In one embodiment, such extensions are minimal—i.e., not more than six additional amino acids—at either the N-terminus or the C-terminus, or distributed between these termini; preferably no more than four total additional amino acids, and most preferably no more than two.

The form of domain B which spans positions of about 296–395 is referred to herein as "classical" domain B. When the B domain includes at least portions of the region extending to amino acid 413, the additional region may confer additional functions, e.g., enhancing immunogenicity by providing a helper T cell epitope. The form of domain B which includes positions about 296–413 is referred to herein as DomB+T. The domain B of the invention includes these two specific embodiments; "classical" domain B and DomB+T, as well as those forms which span positions approximately 296 to position between position 395 and 413.

Other portions of the E protein illustrated below are self-explanatory. 80% E is the N-terminal 80% of the protein from residue 1 to residue 395. 60% E represents the corresponding shorter sequence. These subunits are produced from vectors containing the DNA encoding the mature protein, or along with the prM fusion which results in secretion of the 80% or 60% per se.

For practical large-scale production of the subunits used as active ingredients in the vaccine of the invention, recombinant techniques provide the most practical approach. However, to be useful as active glycosylation, folding, and disulfide bond formation for producing a proper immune response.

It has now been found that the B domain of the envelope protein can be successfully secreted from yeast in a form which elicits the production of neutralizing antibodies. This permits, for the first time, the production of a successful recombinantly produced subunit dengue vaccine.

DISCLOSURE OF THE INVENTION

The invention provides vaccines containing as an active ingredient, a secreted recombinantly produced the dengue envelope protein or a subunit thereof. The vaccines are capable of eliciting the production of neutralizing antibodies against-dengue virus. In the illustrations below, the B domain of the envelope protein (E) is secreted from yeast by producing it in an expression vector containing the α-mating factor prepropeptide leader sequence (preproMFα$_L$). Peptide subunits representing 60% E and 80% E are secreted from Drosophila cells using the human tissue plasminogen activator secretion signal sequence for the propeptide (tPA$_L$) or from the homologous premembrane (prM) leader. The secreted products can easily be purified and prepared as a vaccine.

Thus, in one aspect, the invention is directed to a vaccine for protection of a subject against infection by dengue virus. The vaccine contains, as active ingredient, the envelope protein of a dengue virus serotype or a subunit thereof. The E or subunit is secreted as a recombinantly produced protein from eucaryotic cells. The vaccine may further contain portions of additional dengue virus serotype E proteins similarly produced.

In other aspects, the invention is directed to methods to protect subjects against infection by administering the invention vaccines, to antibodies generated in a mammalian subject administered an immunogenic amount of the vaccine; immortalized B cell lines which generate monoclonal antibodies of this type; methods to effect passive immunization by administering the antibodies of the invention; methods to detect the presence or absence of antidengue virus immunoglobulins utilizing the secreted recombinantly produced peptides of the invention and the recombinant materials important in the secretion of the B domain and methods for its production.

BRIEF DESCRIPTION OF THE DRAWINGS

Figure 1:
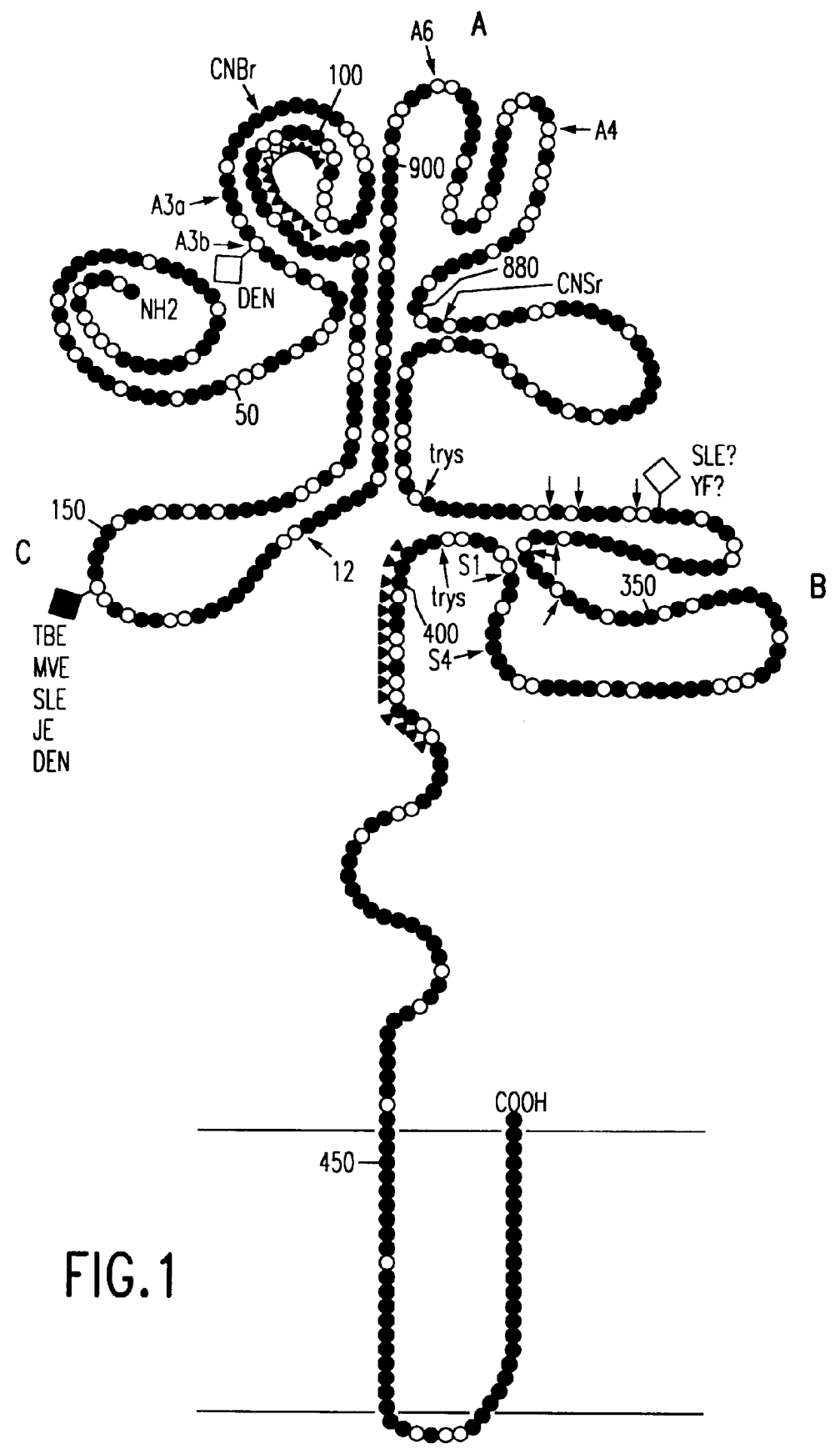

FIG. 1 is a drawing reproduced from Mandl, et al. (supra) showing a model of the envelope protein of flaviviruses. Model of the TBE virus protein E. Open circles represent hydrophilic amino acid residues (Arg, Lys, Asn, Asp, Gln, Glu, His), dotted circles show intermediate amino acid residues (Pro, Tyr, Ser, Trp, Thr, Gly), and solid s circles showed hydrophobic amino acid residuess (Ile, Val, Leu, Phe, Cys, Met, Ala). Amino acids were classified by the scale of Kyte and Doolittle (22). Position numbers are shown every 50 amino acids. Cysteine residues forming disulfide bridges are connected by solid lines. Arrows depict cleavage sites that liberate 1RF1 (tryp.) and 1RF3 (CNBr), respectively. Small arrows indicate potential cleavage sites within these fragments that are not utilized. Two solid lines stand for the lipid membrane that is spanned by two transmembrane regions of protein E. The polypeptide chain is folded to indicate the antigenic domains A, B, and C, which are designated by large capital letters. Arrows together with the names of neutralizing MAbs depicts the locations of the mutations identified in the respective antigenic variants of TBE virus by sequence analysis. A line of solid triangle indicates the almost perfectly conserved sequence with in domain A. A line of open triangles marks the region of a potential T-cell determinant. A solid diamond represents the carbohydrate side chain of TBE virus. The Murray Valley (MVE), St. Louis (SLE) and Japanese (JE) encephalitis viruses and DEN viruses have potential N-glycosylation sites at the homologous position. Yellow fever (YE) and St. Louis encephalitis viruses have such a site within domain B. DEN viruses within domain A. The homologous positions of TBE virus are shown as open diamonds.

FIG. 2 (SEQ ID NO:1) shows the partial nucleotide sequence for DEN-2 PR159 S1 mutant strain and differences from the wild-type strain reported by Hahn (1988, supra). DEN-2 PR159/S1 cDNA coding strand sequence for Capsid, preMembrane, Envelope, and NS1 is given (Hahn etr al. 1988). The start of genes are indicated. "*" indicates correction to published sequence. Difference in the wild-type DEN-2 PR159 sequence are indicated above the PR159/S1 sequence.

FIG. 3 (SEQ ID NO:2 and SEQ ID NO:3) shows the partial nucleotide sequence and deduced amino acid sequence of the genome of DEN-2 PR159/S1 strain in comparison with wild-type.

FIG. 4 (Residues 1693–1752 of SEQ ID NO:1 and SEQ ID NO:4 through SEQ ID NO:7) shows the oligonucleotide used to mutagenize an 80% E cDNA clone to obtain the domain B coding sequence. Shown are the necleotide sequence and the corresponding translation of DEN-2 PR159/S1 E sequences between genomic nucleotides 1789 and 1848, the sequence of the oligonucleotide used in mutagenesis, and the resulting sequence and corresponding translations following mutagenesis. Dengue nucleotide sequence is uppercase, non-dengue nucleotides are longer case, inserted restriction endonuclease sites are indicated, and conserved cysteines are underlined.

FIG. 7 (SEQ ID NO:8 and SEQ ID NO:9) shows the nucleic acid and amino acid sequence of mating factor α leader, preproMFα$_L$/domain B fusion protein.

FIG. 10 shows the survival times of mice immunized with recombinant domain B and challenged with Dengue-2.

MODES OF CARRYING OUT THE INVENTION

Figure 5:
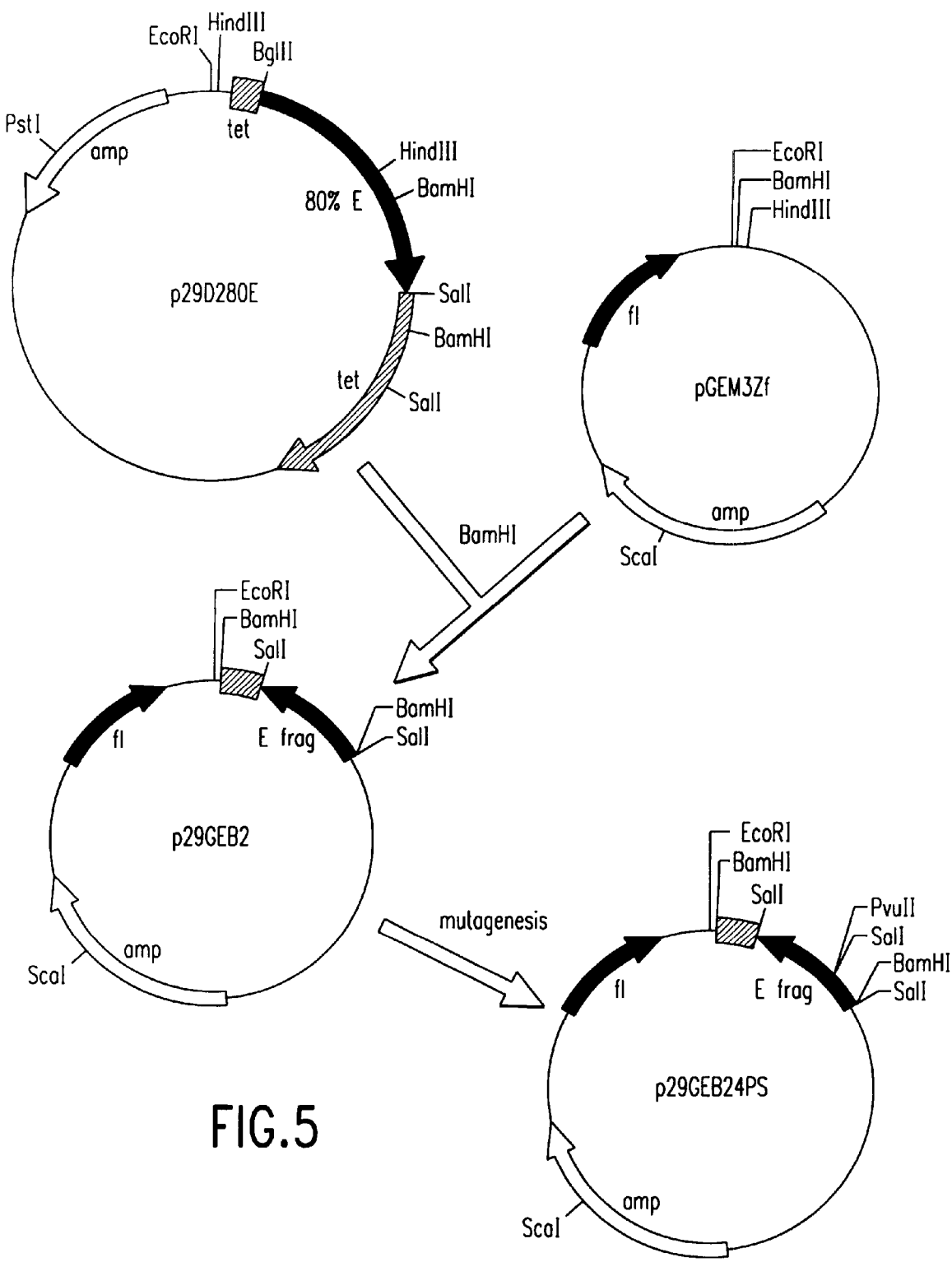
FIG. 5 shows the construction of a cloning vector containing the nucleotide sequence encoding domain B.

The invention provides, for the first time, a subunit vaccine that can be efficiently produced recombinantly and secreted and that is effective in protecting subjects against infection with dengue virus. Although many attempts have been made to obtain such a subunit vaccine, either the subunit itself is resistant to recombinant production techniques which permit it to be secreted in a processed form so as to render it effective as an immunogen, or, if its recombinant production is facile, it fails to elicit neutralizing antibodies. The present inventors have found that certain portions of the envelope protein of dengue virus type 2, such as domain B representing approximately 100 amino acids of the envelope protein extending approximately from the Gly at position 296 to the Gly at position 395, and optionally including additional E sequence through position 413 of the protein, and other portions of E, i.e., 60% E and 80% E are effectively secreted by certain convenient eucaryotic recombinant hosts, in a form that permits processing to mimic the native conformation of the protein. The secretion of the protein into the culture medium facilitates purification. Furthermore, this form is able, when administered, especially in the presence of adjuvant, to raise neutralizing antibodies in animals. Thus, this subunit represents a useful component of a vaccine for protecting subjects against dengue infection.

As used herein, "B domain" refers to a peptide which spans from approximately Gly 296 to Gly 395 of the DEN-2 envelope protein, and optionally including additional E sequence through position 413 of the envelope protein. These positions are approximate; for example, Mandl (1989, supra) describes the generation of a tryptic fragment containing domain B which spans the amino acids of the TBE E protein from position 301 to 396. The sequences described in the present application represent the envelope protein from dengue Type 2 virus (DEN-2); three additional distinct dengue serotypes have been recognized. Therefore, "Domain B" also refers to the corresponding peptide region of the envelope protein of these serotypes, and to any naturally occurring variants. In addition, B domain includes extended forms of the about ingredients, the subunits as produced must assume a conformation and undergo processing under conditions which, render them similar to the native envelope portion as it exists in the envelope protein of the virus. In order to achieve this, the recombinant production must be conducted in eucaryotic cells, preferably yeast or Drosophila cells. In addition to the *S. cerevisiae* in *P. pastoris* yeasts illustrated below, other yeasts, such as Kluveromyces sp *Yarrowia lipolytica,* and *Schizosaccharomyces pombe* may be used. Other insect cells besides the *Drosophila melongaster* Schneider cells illustrated below may also be employed. Additional appropriate eucaryotic cells include mammalian expression cells such as Chinese hamster ovary cells. Other insect cells may also be used in conjunction with baculovirus based vectors. The B domain or 60% E or 80% E must be produced as a correctly processed protein and secreted.

It has been found, as demonstrated hereinbelow, that particularly efficient secretion of biologically active mature protein can be achieved in several ways. First, this can be done by expressing the B domain in yeast in operable linkage with the α-mating factor signal sequence. Constructs which place the nucleotide sequence encoding the B domain disposed so as to encode a fusion protein with an upstream α-mating factor signal sequence are therefore included within the scope of the invention. An additional preferred embodiment employs Drosophila cells and the human tissue plasminogen activator leader sequence for secretion of 60% E or 80% E as well as domain B. Envelope protein subunits that represent N-terminal portions of truncated protein may also be secreted from the homologous prM fusion. Other secretion signal peptides or secretion leader pre/pro peptides, such as those associated with invertase or acid phosphatase of *S. cerevisiae* or with glucoamylase of *C. albicans* or of *A. niger* or the bovine chymosin prepropeptide secretion leader can also be used. Secretion leaders in general that occur at the amino terminus of secreted proteins and function to direct the protein into the cellular secretion pathway generically can be used. In general, the invention includes expression systems that are operable in eucaryotic cells and which result in the formation of envelope protein or a subunit secreted into the medium. Thus, useful in the invention are cells and cell cultures which contain expression systems resulting in the production and secretion of mature B domain.

The properly processed E protein or subunit is recovered from the cell culture medium, purified, and formulated into vaccines. Purification and vaccine formulation employ standard techniques and are matters of routine optimization. Suitable formulations are found, for example, in *Remington's Pharmaceutical Sciences,* latest edition, Mack Publishing Company, Easton, Pa. In particular, formulations will include an adjuvant, such as alum or other effective adjuvant. Alternatively, the active ingredient and the adjuvant may be coadministered in separate formulations.

The active vaccines of the invention can be used alone or in combination with other active vaccines such as those containing attenuated forms of the virus or those containing other active subunits to the extent that they become available. The vaccines may contain only one subunit as an active ingredient, or additional isolated active components may be added. Corresponding or different subunits from one or several serotypes may be included in a particular formulation.

To immunize subjects against dengue fever, the vaccines containing the subunit are administered to the subject in conventional immunization protocols involving, usually, multiple administrations of the vaccine. Administration is typically by injection, typically intramuscular or subcutaneous injection; however, other systemic modes of administration may also be employed. Although the technology is not as well developed, transmucosal and transdermal formulations are included within the scope of the invention as are effective means of oral administration. The efficacy of these formulations is a function of the development of formulation technology rather than the contribution of the present invention.

Since the subunit vaccines containing B domain have been shown to elicit the production of neutralizing antibodies, the antibodies thus raised can themselves be used as passive vaccines. For production of passive vaccine, a suitable mammalian subject is immunized with the E protein or subunit of the invention and antibodies are either recovered directly as a composition from the antisera or indirectly as monoclonal antibodies from immortalized B cells of the subject. For production of monoclonal antibodies, the conventional techniques of Kohler & Milstein, for example, or treatment with Epstein Barr virus, are used in immortalizing peripheral blood lymphocytes or spleen cells and screening for antibodies immunoreactive with the immunogen. These antibodies may further be screened for their ability to effect plaque reduction in infected sera or cultures.

The polyclonal antisera are generally subjected to purification techniques such as standard size separation and chromatographic techniques to obtain purified immunoglobulins. The recombinantly produced proteins of the invention are particularly useful affinity ligands for chromatographic purification. A multiplicity of techniques is available for the purification of immunoglobulins for use in passive vaccines. If monoclonal antibodies are to be purified from small volumes of a medium ascites fluid, a protein A affinity column is particularly useful. For larger volumes, additional standard chemical techniques, such as ammonium sulfate precipitation and DEAE chromatography can be used. These immunoglobulins or the monoclonal antibodies generated by the immortalized B cells are then used in vaccine formulations as is understood in the art.

As is the case with active vaccines, the passive vaccines of the invention may be used in combination with additional antibodies or tandem administration of the antibodies of the invention and additional antibodies may be employed.

In the event that the passive vaccine is intended for use in a species other than that of the subject in which the antibodies were prepared, it may be desirable to modify the antibodies to minimize any immunogenic response. For example, it may be possible to use only the variable regions of these antibodies, such as the $F_{ab}$, $F_{ab'}$, or $F_{(ab')_2}$ regions. These fragments can be prepared either from polyclonal antisera or from the supernatants of hybridoma cultures by treating with proteolytic enzymes and recovering the desired fragments. The fragments are readily separated by using the relevant protein of the invention as an affinity reagent.

Alternatively, chimeric antibodies can be produced wherein the constant region corresponding to the species to be protected is substituted for the constant region characteristic of the species of antibody origin. The availability of recombinant techniques makes the production of chimeric antibodies a relatively trivial exercise. Briefly, a hybridoma or cell line producing the antibody of interest is used as a source for the genes encoding the antibody. The genes are recovered from, for example, the hybridoma using standard cloning procedures. The genes are then manipulated in vitro to remove the constant region and replace it with a constant region of a different species origin. The modified genes are then ligated into expression systems and expressed in recombinant host cells, such as CHO cells, monkey cells, yeast cells, and the like.

Further modifications in the variable regions can also reduce immunogenicity. Again, since recovery of the genes encoding the antibody is within the skill of the art, the variable regions, too, can be manipulated to replace the framework regions with framework regions more representative of the desired species, leaving intact the complementarily determining regions responsible for antigen specificity. In still another embodiment, the variable heavy chain and variable light chain regions can be linked through a peptide linker and produced as a single chain $F_v$ molecule.

Thus, if the passive vaccines are intended for humans, the foregoing various techniques of humanizing antibodies can be employed to minimize any immunogenic response even though the original antibodies are raised in nonhuman species.

In addition to use in vaccines or in the generation of passive vaccines, the mature recombinant E protein and subunits of the invention may be used as analytical reagents in assessing the presence or absence of antidengue antibodies in samples. The interest in doing this may be diagnosis of infection with dengue, monitoring response to dengue infection or may simply reside in the use of immunoassays as part of standard laboratory procedures in the study of the progress of antibody formation or in epitope mapping and the like. The antigen is employed in standard immunoassay formats with standard detection systems such as enzyme-based, fluorescence-based, or isotope-based detection systems. Preferably, the antigen is used coupled to solid support or in sandwich assays, but a multiplicity of protocols is possible and standard in the art.

Thus, the secreted protein, such as 60% E, 80% E or B domain may be adsorbed onto solid support and the support then treated with a sample to be tested for the presence of antidengue antibodies. Unbound sample is removed, and any bound antibodies are detected using standard detection systems, for example, by treating the support with an antispecies antibody with respect to the species represented in the sample to be tested, the antispecies antibody coupled to a detection reagent, for example, horseradish peroxidase (HRP). The presence of the HRP conjugated antispecies antibody is then detected by supplying a suitable chromogenic substrate.

Alternatively, the anti-subunit or antidengue antibody may be adsorbed to the solid support and detected by treating the solid support with the recombinant domain B, either directly labeled, or labeled with an additional antibody in a sandwich-type assay.

In addition, both the mature peptides, such as domain B and 60% E or 80% E of the invention and the antibodies immunoreactive with it can be used in standard purification procedures as affinity reagents. Thus, purification of the subunits from recombinantly produced cultures can be effected by affinity columns using antibodies raised against these antigens. Conversely, immunoglobulins useful in passive vaccines can be readily purified from antisera using the peptides of the invention.

The mature domain B or other subunit of the invention may be used to detect the presence or absence of antibodies of various isotypes, including IgG and IgM isotypes. As set forth above, detection of IgM isotypes is significant since this is an index of primary infection.

In the examples below, particular subunits of the dengue Type 2 envelope protein, in particular 60% E, 80% E and domain B are illustrated as representative of effective subunits of the envelope protein. For the 60% E and 80% E constructs in general, secretion can be obtained from constructions designed to express the prME subunit fusion. The mature N-terminus of the envelope protein is then secreted into the culture medium. Whether the N-terminus of the envelope protein subunits were fused to a heterologous leader, such as the human tissue plasminogen activator leader sequence, or to the homologous prM sequence, the mature form of the truncated envelope protein is secreted. The secreted truncated Es are expressed at high levels in Drosophila, efficiently processed, and secreted into the medium. The products are glycosylated and processed to an endo-H resistant form. The secreted form of truncated E produced cotranslationally with prM generally represents about 20–30% of the total protein in the medium. Furthermore, based upon reactivity with conformationally sensitive monoclonal antibodies, using a ELISA and immunofluorescence formats, the secreted E products are shown to have a native conformation. Immunization of mice with crude medium from transformed cells expressing prM-truncated E induces a potent virus-neutralizing response.

The following examples are intended to illustrate but not to limit the invention.

EXAMPLE 1

Preparation of Envelope Proteins in *Saccharoimyces cerevisiae*

A cDNA clone derived from dengue serotype 2 (DEN-2) described by Hahn, Y. S. et al. *Virology* (1988, supra) was used as the starting material. This cDNA derives from strain PR159/S1. This strain has a small plaque, temperature-sensitive phenotype; the complete sequence of the CDNA derived from the genomic RNA for PR159/S1 is set forth in this publication.

FIG. 2 shows the sequence of the CDNA derived from genomic RNA of DEN-2 PR159/S1 for the Capsid, preMembrane, Envelope, and NS1 genes. Shown in bold at nucleotides 103, 1940, 1991, and 2025 are corrections to the Hahn published sequence. Differences in the S1 sequence from the wild-type sequence are noted above the wild-type sequence. There are no nucleotide differences in the Capsid and preMembrane protein-encoding portions and there are four in the E encoding portion.

FIG. 3 shows the cDNA sequence of DEN-2 PR159/S1 for the Capsid, preMembrane, Envelope, and NS1 genes and the inferred translation of those four genes, which is part of the larger dengue polyprotein. The four differences between wild-type DEN-2 PR159 and the S1 strain are shown above the S1 nucleotide sequence. Also shown is the context of the codons in which the nucleotide differences occur and the encoded amino acid.

In the E gene, three of the four mutations are silent; S1 has G instead of A at position 1314, T rather than G at position 1356, and C rather than T at position 2025. The mutation at position 1858, a G in S1 rather than A, results in a coding change from Ile in wild-type to Val in S1. There is, therefore, a one amino acid difference in the B domain in the S1 strain as compared to wild-type. Although the amino acid substitution conferred by the mutation at 1858 is conservative, mutagenesis studies of other viral structural proteins (Coller, B. G. et al. (1994) *Mutagenesis Studies on the Predicted VP2 E-F Loop of Coxsackievirus B3*, Abstract, 13th Annual Meeting of the American Society for Virology) have demonstrated that even relatively conservative single amino acid changes in surface loops can have profound effects on viral biology, including infectivity and viral stability. Thus, it is not without foundation that the conservative mutation in domain B of DEN-2 PR159/S1 may be involved in the attenuation of this small-plaque, temperature-sensitive variant.

Subsequent determinations on the S1 strain used herein (S1/HBG) showed that the A at position 103 in wild-type was retained in position 103 in S1/HBG and C was substituted for T at position 2025 (a silent mutation). A deduced amino acid sequence from DEN-2 PR159/S1 and differences occurring in the wild-type are shown in FIG. 3.

Various E gene subclones were obtained which represented the amino-terminal 90% of the envelope, 80% of the envelope, 60% of the envelope and classical domain B. Using the assignment of Mandl, C. W. et al. *J Virol* (1989) 63:564–571, classical domain B starts at Gly296 and ends at Gly395. Classical domain B contains only one disulfide bond and is encoded by the sequence following domains A and C. This classical domain B does not contain the potential T cell epitope described by Mandl et al. at its carboxy end which can be included in some forms of the domain B of the invention, e.g., DomB+T.

The portion of the genome that encodes 80% of the envelope protein (80% E) was amplified using the Polymerase Chain Reaction, primers D2E937p and D2E2121m, and plasmid pC8 (Hahn et al. (1988, supra) as template.

In this notation of the primers, the virus serotype is first indicated (D2 for DEN-2), then the corresponding dengue gene—i.e., in this case envelope, E, is noted. Then is noted the number in the dengue cloned sequences of FIGS. 2 or 3 for the first dengue nucleotide in the 5'-3' direction of the oligonucleotide, i.e., using the numbering of Hahn et al. (1988, supra), and finally the notation shows whether the oligonucleotide primes the plus (p) or the minus (m) strand synthesis. The sequence in the primers corresponding to dengue cDNA are written in uppercase letters; nondengue sequence is written in lowercase letters.

```
D2E937p2

BglII
5'-cttctagatctcgagtacccgggacc ATG CGC TGC ATA GGA ATA TC-3' (SEQ ID NO:13)
      XbaI   XhoI    SmaI D2E2121m SalI
5'-gctctagagtcga cta tta TCC TTT CTT GAA CCA G-3'          (SEQ ID NO:14)
      XbaI       End End
```

The D2E2121m primer placed two stop codons after the 395th codon of E. The 80% E amplified cDNA fragment was digested at the XbaI sites in the cloning adapters and cloned into the NheI site of pBR322 to obtain p29D280E. Double-strand sequence for 80% E was determined, which identified a single silent PCR-introduced mutation at nucleotide 2001 (AAC/Asn to AAT/Asn).

A subclone representing domain B was obtained from the 80% E subclone by oligonucleotide-directed mutagenesis. In the mutagenesis, stop codons and restriction endonuclease sites were inserted between domain C- and domain B-encoding sequences. The stop codons were positioned to terminate domain A+C translation and SalI and PvuII restriction sites were added to facilitate subcloning of domains A+C and domain B fragments, respectively, into yeast expression vectors. As shown in FIG. 4, to avoid a high AT content in the mutagenic oligonucleotide, the stop codons defining the carboxy-terminus of 60% E containing domains A and C were positioned four codons upstream of the beginning of domain B, i.e., following Lys291. The original and altered nucleotide sequences of the mutagenized region and the corresponding amino acid translation are shown in FIG. 4.

To perform the mutagenesis, a 580 bp BamHI fragment spanning domain B from the pBR322–80% E clone p29D280E was subcloned into pGEM3Zf (Promega) to yield p29GEB2. (See FIG. 5.) This BamHI fragment encodes the 3' end of domains A and C and all of domain B. The plasmid obtained following mutagenesis, p29GEB24PS, was confirmed by DNA sequencing. As shown in FIG. 6, the introduced PvuII site permits direct subcloning of domain B CDNA into yeast expression vectors as a fusion with yeast secretion leader.

The cloned cDNA fragments encoding B domain and 80% E were inserted into expression vectors so as to maintain the translational frame of fusions to secretion leaders as described below. The sequence of the fusions were confirmed by DNA sequencing.

EXAMPLE 2

Secretion of Domain B from *Saccharomyces cerevisiae*

The expression vector constructed to secrete classical domain B from *Saccharomyces cerevisiae* to include envelope protein amino acids 296–395 was constructed so that processing by the proteases normally involved in prepro$MF\alpha_L$ processing would yield a precisely processed domain B. One of these proteases, Kex2p, the gene product of the Kex2 gene, cleaves following dibasic peptides, such as LysArg, LysLys, ArgArg, and ArgLys. A second protease involved, a dipeptidyl amino peptidase, removes GluAla and AspAla dipeptides from the amino terminus after Kex2p processing.

Figure 6:
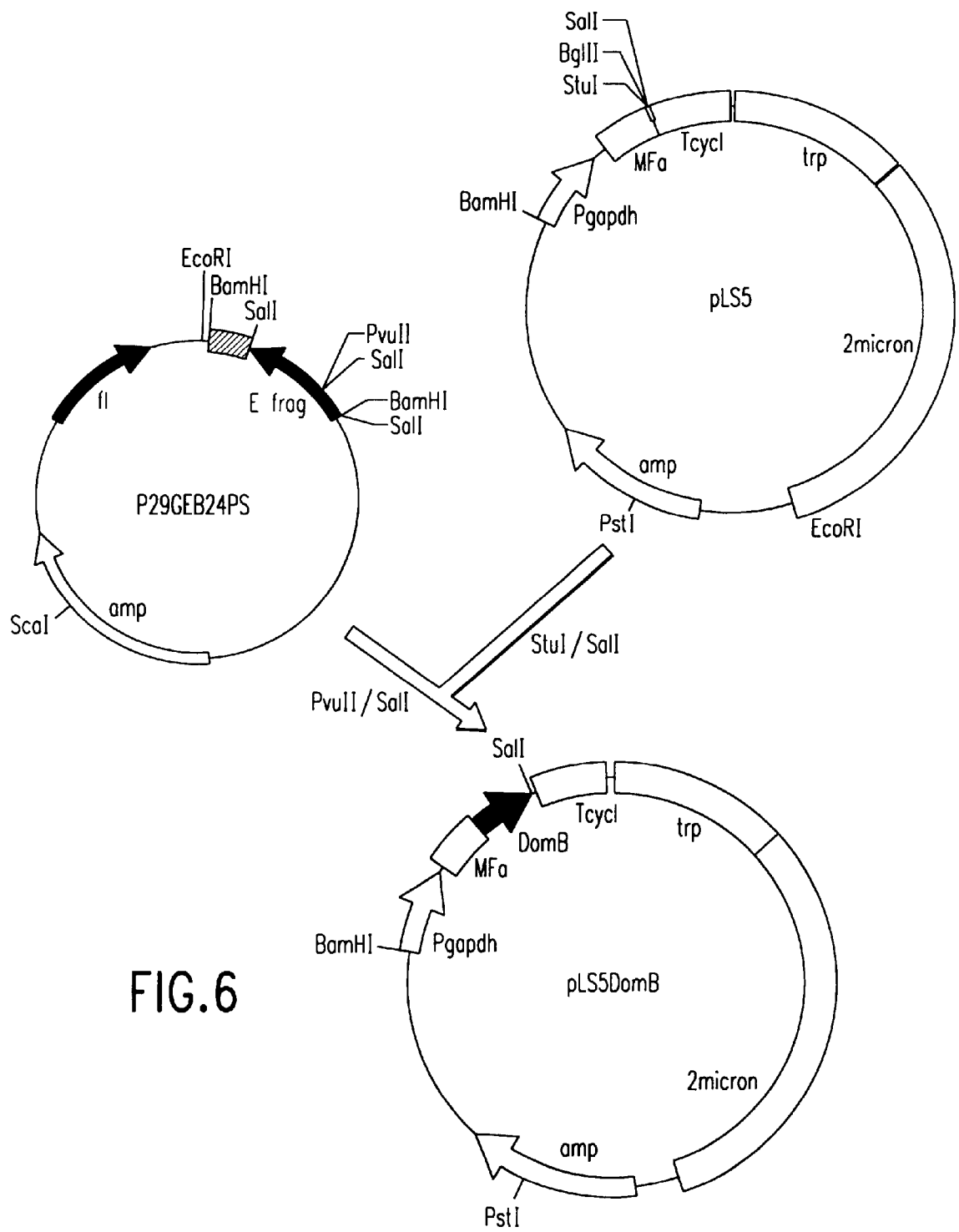
FIG. 6 shows the insertion of the domain B coding sequence into the yeast expression vector pLS5.
Figure 8:
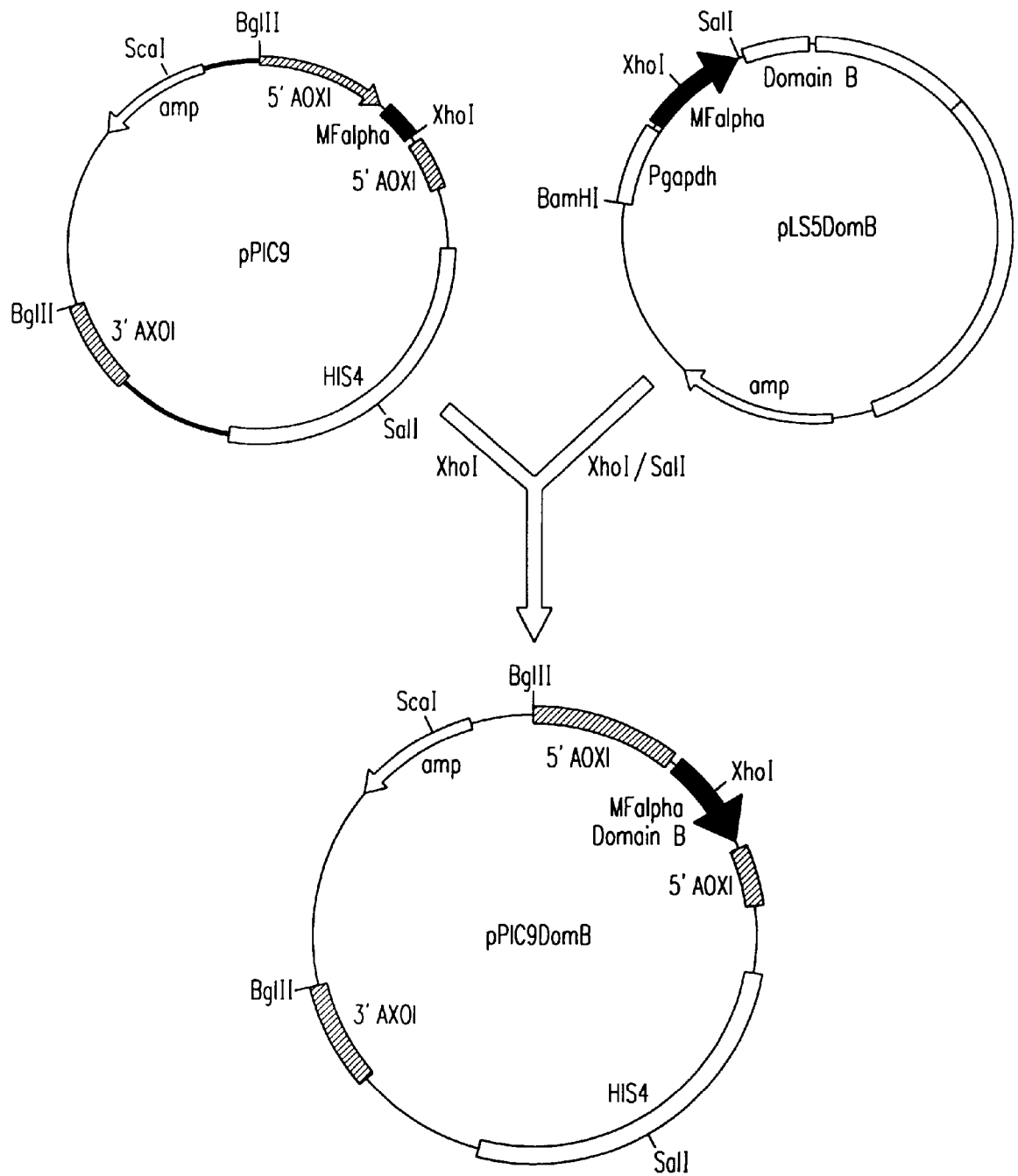
FIG. 8 shows the construction of an expression vector for domain B in Pichia.
Figure 9A:
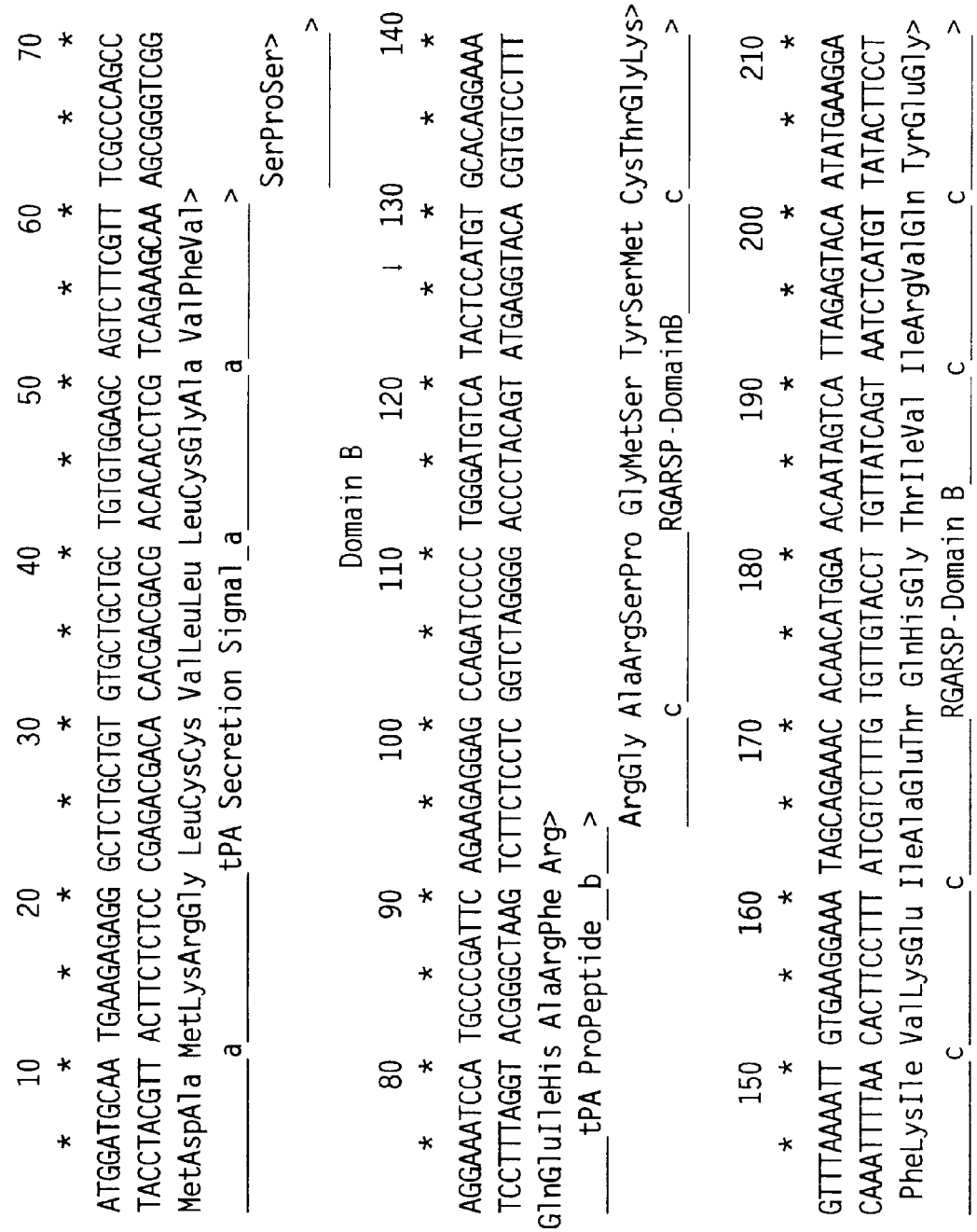
FIG. 9 (SEQ ID NO:10 through SEQ ID NO:12) shows the nucleotide and deduced amino acid sequence for the tPA$_L$-DomB fusion protein.
Figure 11:
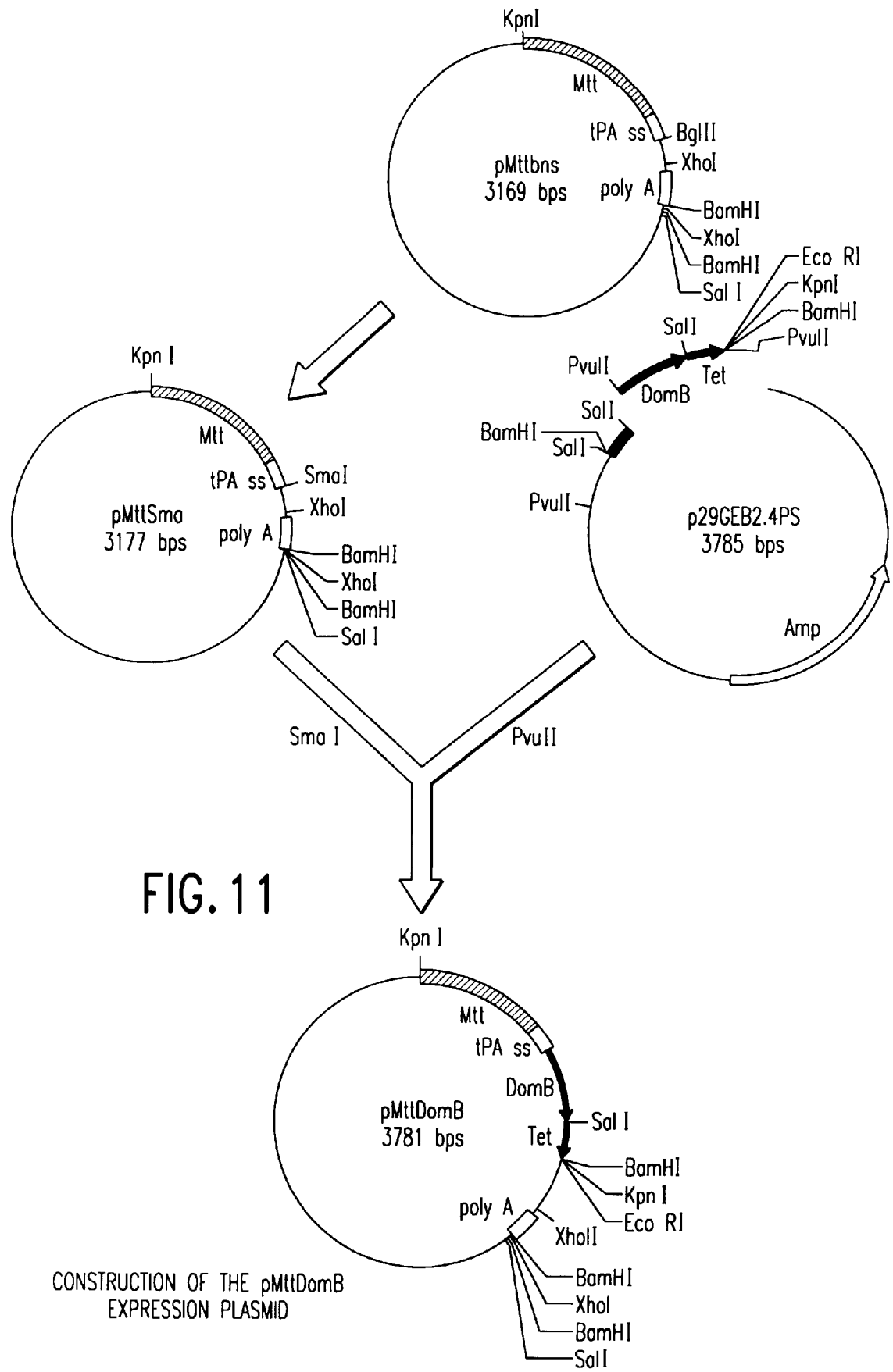
FIG. 11 shows the construction of an expression vector for production of domain B in *Drosophila melanogaster* tissue cultured Schneider cells.
Figure 12:
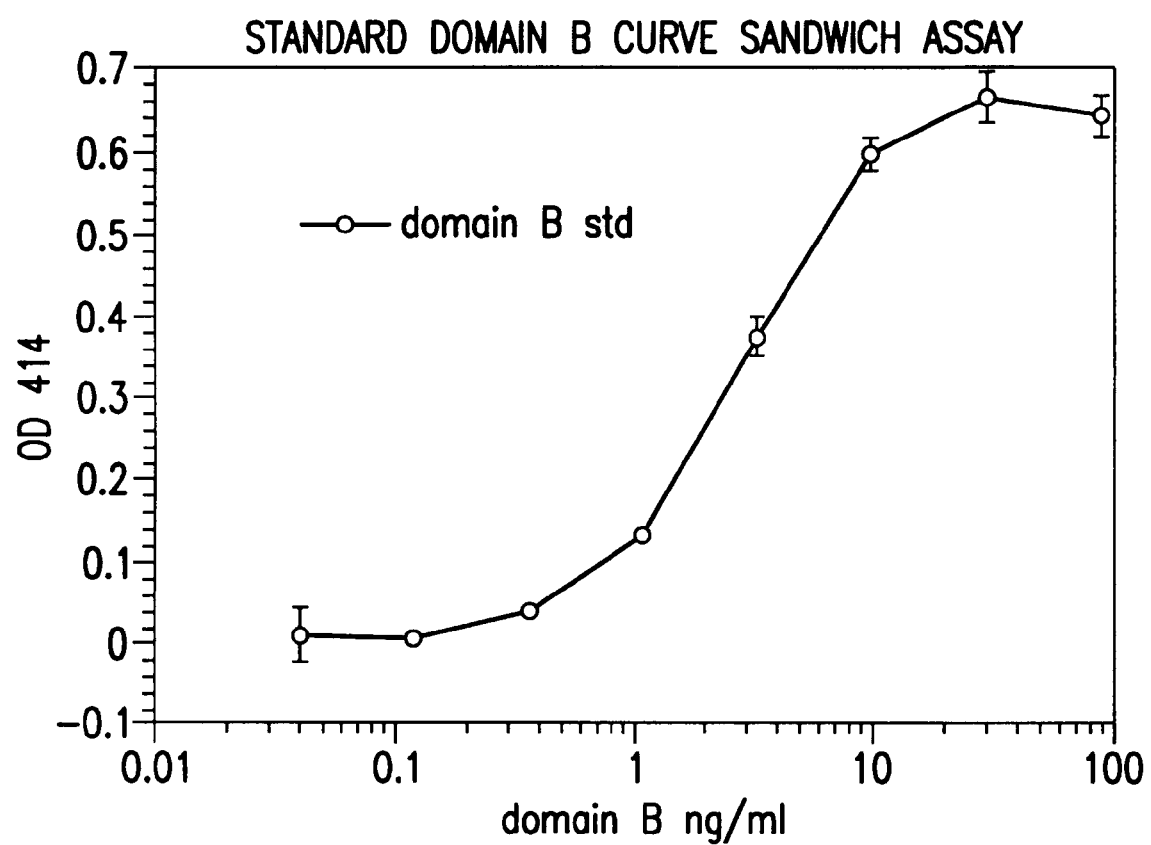
FIG. 12 shows the standard curve for a DomB sandwich assay.

The MFα prepropeptide (MFα$_L$)-domain B fusion was operably linked to the constitutive promoter from the gene (TDH3) encoding glyceraldehyde phosphate dehydrogenase (GAPDH) contained in pLS5 and, alternatively, to the copper sulfate-inducible CUPI gene promoter contained in pLS6. These vectors were provided by SmithKline Beecham. Both contain the MFα$_L$ sequence, and StuI, BglII, and SalI cloning sites, and use the TRP1 gene as a selectable marker. They contain sequences derived from pBR322 to provide an E. coli origin of replication, the ampicillin resistance gene, and sequences derived from the 2-micron plasmid of S. cerevisiae to enable replication in S. cerevisiae. The insertion of the classical domain B coding sequence into the appropriate reading frame in pLS5 was accomplished by digesting pLS5 with StuI and SalI and by digesting p29GEB24PS with PvuII and SalI and gel purifying the small PvuII-SalI domain B fragment and ligating it into the thus opened pLS5 as shown in FIG. 6. A domain B expression vector derived from pLS6 was constructed in a similar manner.

The nucleotide and amino acid sequence of the MFα$_L$-domain B fusion is shown in FIG. 7.

The resulting expression vectors were transfected into spheroplasts of Saccharomyces cerevisiae strain GL43 (MATatrp1Δ1 ura3-52 proA::URA3) and transformants were selected by their ability to grow on minimal medium without tryptophan supplementation. S. cerevisiae strain GL43 was supplied by Smith-Kline Beecham. Strain GL43 pLS5-DomB and pLS6-DomB transformants were grown in small (<5 ml) cultures i Casamino acid-supplemented minimal medium, and proteins secreted into the culture medium and cellular proteins were analyzed by Coomassie-stained SDS-PAGE and Western blot. A novel Coomassie-staining band of approximately 12 kD, which was weakly immunoreactive with DEN-2 HMAF, was observed in the culture media of domain B transformants. No novel Coomassie-staining bands and little or no immunoreactive protein not found in negative controls was observed in cellular protein extracts of domain B transformants. When cultured in Casamino acid supplemented minimal medium, comparable levels of domain B were secreted into the medium by pLS5-DomB and pLS6-DomB transformants. About 20% of the total secreted protein was domain B as estimated by the intensity of Coomassie brilliant blue staining of protein in an SDS-PAGE polyacrylamide gel.

The composition of the medium was optimized; when *S. cerevisiae* containing pLS5-DomB were grown in minimal medium (SD) or Casamino acids (Difco)-supplemented. minimal medium, the yields of protein were less than when cultured in rich (YEPD) medium. The pLS5-domain B transformant was preferred since this transformant can be cultured in rich medium whereas pLS6-domain B transformants require the use of the less preferred supplemented minimal medium in order to induce with copper sulfate.

The secreted protein was confirmed as domain B having a Glu-Ala dipeptide appendage to the N-terminus, designated herein Glu-Ala-Domain B or Glu-Ala-DomB. For this demonstration, proteins secreted by a pLS5-DomB transformant were separated by SDS-PAGE and electroblotted to Immobilon P membrane (Millipore), and the amino terminal amino acid sequence was determined by microsequencing. That sequence is: $H_2N$-Glu Ala Gly Met Ser Tyr Ser Met Xxx Thr Gly Lys Phe Xxx Val Val (SEQ ID NO:15). The persistence of the GluAla dipeptide indicates that the dipeptidyl aminopeptidase incompletely processed the domain B N-terminus following proteolysis by Kex2p.

EXAMPLE 3

Purification of Domain B

A. Initial Purification Method:

Pilot purifications of domain B from *S. cerevisiae* culture medium used size exclusion chromatography on acrylamide Biogel P100.

For these purifications, an *S. cerevisiae* GL43 pLS5-DomB transformant was cultured in minimal medium overnight and then transferred to either Casamino acid-supplemented minimal (SD) medium or rich (YEPD) medium for expression. After culturing at 30° C. for 2–3 days and feeding daily with buffered glucose to final concentrations of 0.4% glucose and 5 mM sodium phosphate (pH 6.7), the cells were pelleted by centrifugation and the medium was clarified by filtration through a 0.45 μm pore filter. The filtered medium was concentrated about 30-fold either by tangential flow or by centrifugal ultrafiltration using Minitan (Millipore) or Centricon (Amicon) devices, and the concentrate was exchanged into PBS azide buffer (2.7 mM KCl, 1.2 mM $KH_2PO_4$, 138 mM NaCl, 4.3 mM $Na_2HPO_4 \cdot 7H_2O$, 0.02% azide) by diafiltration or dialysis.

In one example, the concentrated secreted proteins from approximately 500 ml of culture of GL43 pLS5-DomB grown in SD plus Casamino acids were loaded onto a 2.5×75 cm Biogel P100 column and domain B was eluted from the column at approximately 1 bed volume. Domain B was pooled based on SDS-PAGE analysis of column fractions. The pooled domain B fractions were brownish in color and could not be decolorized by dialysis. The brown colored preparation also was not immunoreactive in ELISAs. DEAE chromatography of this sample resulted in binding of the brown color and a mostly colorless flow-through containing domain B. For DEAE chromatography, the brown-colored pooled fractions were dialyzed against 0.1 M acetic acid, pH 5.1 and loaded onto a 1.4×15 cm DEAE (Biorad) column. Domain B was eluted using a 0.01 M acetic acid, pH 5.1, 0.1 M NaCl step gradient.

The purified domain B was of high purity as assessed by silver stain on SDS-PAGE. The resulting Glu-Ala-DomB also gained weak reactivity with antidengue mouse polyclonal HMAF and with antidengue MAbs 3H5 and 9D12 in an ELISA format. The reactivities of earlier colorless preparations from smaller cultures were greater than this initial large-scale preparation. For the ELISA, 96-well microtiter plates were coated with domain B by overnight incubation at 4° C. and then blocked with BSA in 50 mM tris-HCl, pH 7.0, 0.15 M NaCl, 0.05% Tween for 1 hour at room temperature. The plates were then treated with either DEN-2 HMAF or monoclonal antibody. Bound antibody was detected with alkaline phosphatase conjugated goat anti-mouse IgG and measured by the increase in optical density at 414 nm using the alkaline phosphatase substrate paranitrophenylphosphate.

The domain B frequently eluted from the Biogel P100 in two equal fractions, the first with the bulk of the secreted yeast proteins and the second as 70–90% pure domain B. Treatment with 1M NaCl, 1 and 2 M urea, and 1% DDAPS, a zwitterionic detergent, were ineffective in completely disaggregating domain B during size exclusion chromatography. Since the domain B of both fractions had the same electrophoretic mobility in the presence of detergent and absence of DTT, this polypeptide was neither covalently cross-linked to another protein nor self-polymerized via disulfide bonds.

B. Improved Purification Method:

A standard culture and purification method was developed that has reproducibly yielded immunoreactive domain B expressed and secreted by S. cerevisiae GL43 pLS5-DomB. For that method, a primary culture is prepared by inoculating 60 ml of SD medium in a 250 ml baffled flask with a single colony of yeast strain GL43 pLS5-DomB grown on an SD plate. SD medium is prepared by autoclaving 0.67% Bacto yeast nitrogen base without amino acids, cooling and providing 2.0% w/v dextrose and 12 mM $K_2HPO_4$ using autoclave stock solutions. Solid SD medium is prepared by including Bacto agar at 1.8%. The culture is grown at 30° C. for 18–24 hours with shaking at 240 rpm.

Secondary cultures are then grown in 300 ml of SD medium supplemented with 0.2% casamino acids in 2 L baffled flasks. The secondary cultures are inoculated with 30 ml of the primary culture. The secondary cultures are incubated at 30° C. for 18–24 hours with shaking at 300 rpm.

Large-scale tertiary cultures are then prepared by inoculating 1 L of YEPD medium in a 4 L baffled flask with 100 ml of the secondary culture. YEPD is prepared by autoclaving 1% yeast extract plus 2% Bactopeptone, to which sterile dextrose is added to a final concentration of 2% after cooling. The large-scale cultures are incubated at 30° C. for 48 hours with shaking at 300 rpm. After 24 hours, the culture is supplemented with 0.01 vol of sterile 40% w/v glucose and 0.02 vol of sterile 1 M phosphate buffer, pH 6.7.

After growth in the 1 L culture, the cells are removed by centrifugation at 5,000 rpm at 4° C. for 5 min. in a Sorvall GS-3 rotor. EDTA and EGTA are added to final concentrations of 1 mM each to the cleared medium, and the resulting solution is filter sterilized using a 045 μm pore filter membrane (Millipack-20 or Opticap-50, Millipore). Glycerol is added to 10% v/v to the filtrate which is then concentrated 20–30 fold using tangential flow ultrafiltration (Millipore Minitan System) with two membrane cartridges (four regenerated cellulose membranes) of a 10 kD MW cutoff. The retentate is kept on ice during ultrafiltration in the coldroom at 4° C. for about 10–15 hours.

The concentrated medium is directly used or rapidly frozen on dry ice/ethanol in 10 ml aliquots in 15 ml polypropylene or polystyrene tubes with a screw cap and stored at −70° C.

Concentrated medium of the tertiary culture is dialyzed at 4° C. using a membrane with a 6–8 kD cutoff (Spectra/Pore-1 Membrane) against 10 mM acetate, pH 4.5 (4×4 liters; 2–3 hours each; 1 overnight).

For purification, the concentrated, buffer-exchanged medium is loaded onto a 2.5×22 cm CM Biogel A (Biorad) column at 0.8 ml/min. at 4° C. The column is washed with 150–250 ml of 10 mM acetate, pH 4.5 until the optical density at 280 nm of the eluent drops to baseline. Domain B is then eluted with 10 mM acetate, 300 mM NaCl, pH 4.5 at 0.8 ml/min. Fractions of approximately 8 ml are collected and analyzed by SDS-PAGE (15%) and visualized by silver staining. Domain B migrates on the trailing edge of the main peak of eluted material as monitored by 280 nm.

The domain B-containing fractions are pooled and concentrated about 11-fold by centrifugal ultrafiltration using, for example, a Centriprep-10® (brand membrane ultrafiltration system) (Amicon) and loaded onto a 5×60 cm Sephadex G-75® (brand polysepharose) (Superfine, Pharmacia) column at 4° C. The column is eluted using phosphate-buffered saline (PBS: 8 g/l NaCl, 0.2 g/l KCl, 1.44 g/l $Na_2HPO_4$, 0.24 g/l $KH_2PO_4$) at a flow rate of 0.8 ml/min. Nine ml fractions are collected and analyzed by SDS-PAGE as above and by indirect ELISA as above using Mab 9D12.

The Sephadex G-75® (brand polysepharose) fractions containing pure immunoreactive domain B from 2–4 purification runs are concentrated about 50-fold by centrifugal ultrafiltration using a Centriprep-10® (brand membrane ultrafiltration system) (Amicon; final volume 2–5 ml). The pooled material is stored at 4° C.

Glu-Ala-DomB purified as above typically is immunoreactive with the virus-neutralizing monoclonal antibodies 3H5 and 9D12. The above-described culturing and purification protocol has been performed several times with reproducible results. The number of cultures of the above-indicated volumes can be increased, and we have grown simultaneously up to six 1 L tertiary cultures. The culture medium from the multiple cultures is pooled for clarification and concentration, and domain B from the concentrate is purified in batches and pooled following verification of immunoreactivity. The amount of protein in the purified domain B preparations may be quantitated by total amino acid analysis using HCl hydrolysis with on-line ninhydrin reaction and optical detection. Table X presents the yield of protein in purified domain B from four cultures.

TABLE A

Total protein yields in purified domain B preparations

| Lot No. | Culture Volume | Final Yield* | Yield mg/l |
|---|---|---|---|
| 198.76 | 850 ml | 4 mg | 4.7 |
| 198.71 | 1500 ml | 35 mg | 23 |
| 244.68 | 5750 ml | 90 mg | 16 |
| 244.190 | 5000 ml | 25 mg | 5 |

*Based on amino acid composition of total protein.

EXAMPLE 4

Production of Domain B in *Pichia pastoris*

In addition to *Saccharomyces cerevisiae* as used in the previous examples, the methylotrophic budding yeast *P. pastoris* was used as a host. The domain B coding sequence was subcloned into the expression vector pPIC9 (Invitrogen, San Diego, Calif.) which contains the alcohol oxidase (AOX1) promoter sequence from *P. pastoris,* the MF$\alpha$ prepropeptide secretion leader from *S. cerevisiae,* the AOX1 transcriptional termination sequence, and the HIS4 gene from *S. cerevisiae* as a selectable marker. To construct pPIC9-DomB, the domain B-encoding XhoI-SalI fragment from pLS5DomB was inserted into XhoI-digested pPIC9 as shown in FIG. 8. XhoI cuts at identical positions within the MF$\alpha_L$-encoding DNA of both pLS5 and pPIC9, and SalI cuts immediately following the translational stop codons following domain B-encoding sequences. After verification by DNA sequence analysis, the expression cassette, consisting of the AOX1 promoter-MF$\alpha_L$-domain B-AOX1 terminator, plus HIS4 was released from pPIC9-DomB by BglII digestion and the linear DNA was transformed into competent *P. pastoris* cells according to the supplier's instructions (Invitrogen, San Diego, Calif.). Transformants were selected for the ability to grow on medium lacking histidine (His$^{\pm}$ phenotype), and specific integration of the transforming DNA at the AOX1 locus was indicated in some transformants by slow growth on medium containing methanol (Mut$^{s}$ phenotype) as the sole carbon source.

The expression and secretion of domain B from eleven *P. pastoris* pPIC9-DomB transformants in 3 ml cultures was surveyed by Coomassie-stained SDS-PAGE analysis. A protein of molecular weight equal to domain B secreted by *S. cerevisiae* was evident in the culture media of ten of the eleven *P. pastoris* transformants. Immunoblots of a comparable polyacrylamide gel demonstrated that the protein secreted by *P. pastoris* pPIC9-DomB transformants was immunoreactive with polyclonal antibodies made to domain B secreted by *S. cerevisiae* (see Example 6). The SDS-PAGE analysis indicated that *P. pastoris* secreted domain B at a level comparable to or higher than that achieved in *S. cerevisiae*.

For further comparison of the secreted expression levels of domain B by *S. cerevisiae* and *P. pastoris*, the *S. cerevisiae* transformant and the two best *P. pastoris* transformants, Nos. 5–8 (Mut$^±$) and 6–16 (Mut$^s$), were cultured in 100 ml shake flask cultures. *S. cerevisiae* pLS5-DomB was cultured 48 hrs in YEPD medium, and 100 ml precultures of the *P. pastoris* pPIC9-DomB transformants were grown in BMGY medium (1.34% yeast nitrogen base without amino acids, 2% Bacto peptone, 0.4 μg/ml biotin, 1% glycerol, and 100 mM potassium phosphate, pH 6.8) for 24 hrs and then harvested and resuspended ni 25 ml of BMMY heterologous protein-inducing medium (the same as BMGY, except with 0.5% methanol replacing the glycerol) and cultured 48 hrs. Culture media with cells removed by sequential centrifugation and filtration through a 0.45 μm pore size membrane were buffer exchanged by diafiltration into TEEN (10 mM Tris, pH 8.0, 1 mM EDTA, 1 mM EGTA, and 150 mM NaCl). The relative levels of domain B secreted by the three cultures were estimated by size fractionating the proteins in 3, 6, 9, and 12 μl of each sample on a 15% SDS-PAGE gel and staining with Coomassie blue. As estimated by the intensity of Coomassie staining, *P. pastoris* secreted at least four-fold more domain B per volume of induction culture medium than *S. cerevisiae* in YEPD. Correcting for the four-fold concentration of culture volume of the *P. pastoris* when transferred into the induction medium, we conclude that *P. pastoris* secretes slightly more than *S. cerevisiae* in shake flask cultures on a per volume basis. However, on a per gram cell dry weight basis, *P. pastoris* (0.80 gm total cell dry weight) secreted approximately 1.6-fold more domain B than *S. cerevisiae* (1.33 gm total cell dry weight).

EXAMPLE 5

Effect of Extending Domain B

In a manner similar to that set forth in the preceding examples, two plasmid constructs for expression in *S. cerevisiae* were made that include additional domain B-carboxy terminal sequence downstream of amino acid 395 with the domain B coding sequence. One construct, designated DomB+stem, represents Gly296-Gly445 and was expressed as a fusion with the $MF\alpha_L$. This construct includes those sequences that lie between domain B and the transmembrane anchor of E. This region contains a potential T cell epitope (Mandl et al. *J Virol* (1989) 63:564–571) and additional hydrophobic sequences, a peptide from this region elicits virus-recognizing antibodies (Roehrig et al. 1922 in *Vaccines* 92, pp. 2777–2281), and this region may contribute to the proper folding and presentation of the domain B B-cell epitope to the immune system.

The domain B+stem cDNA fragment was constructed in *E. coli* cloning vectors by combining the domain B cDNA fragment and the 3' end of a 90% E clone. As introduced in Example 1, an E gene subclone representing the amino terminal 90% of E was constructed from DEN-2 PR159/S1 cDNA plasmid pC8 of Hahn et al. (1988, supra) using the PCR. The 90% E polypeptide contains all of E except for the C-terminal membrane anchor comprising two transmembrane domains. The 90% E cDNA clone was made as follows. The 90% E fragment was amplified by the PCR using pC8 as template and primers D2E937p and D2E2271m. The sequence of D2E937p is given in Example 1. The sequence of D2E2271m is:

D2E2271m:

```
                                        (SEQ ID NO:16)
          SalI
5'-gctctagagtcga cta tta CCC GTA GAT TGC TCC G-3'
     XbaI       End End
```

Primer D2E2271m placed two stop codons after Gly445 of #, and the two primers positioned useful restriction enzyme sites at both ends of the fragment. The PCR-amplified 90% E cDNA fragment was made blunt at both ends and cloned into the SmaI site of a modified pUC13 cloning vector, yielding pVZ90E.

Combining domain B and the 90% E 3' end made use of a unique Af1III restriction enzyme site found in most pUC-like cloning vectors and a unique Af1III site in domain B sequences. This combining was accomplished by first subcloning the 90% E fragment from pVZ90E into pBluescript to reverse the orientation of 90% E relative to the vector sequences, yielding pBS90E. Then, p29GEB24PS, containing domain B sequences in PGEM (Example 1), and pBS90E were digested with Af1III, and the vector-domain-B5' fragment and the domain-B3'-stem-vector fragment from the two digestions, respectively, were purified, ligated, and recovered in *E. coli* yielding pBS-Bstem.

For expression in *S. cerevisiae,* the PvuII-SalI domain B+stem fragment from pBS-Bstem was subcloned into the pLS5 yeast expression vector at its StuI and SalI sites, putting the $MF\alpha_L$ and B+stem in translational frame. The sequence of the ligated junctions were verified by DNA sequence determination. The domain B+stem expression vector, pLS5-BStem, was transformed into *S. cerevisiae* strain GL43. The resulting transformants grew more slowly than did transformants with pLS5-DomB containing classical DomB and the plasmid appeared to be rapidly lost during growth under nonselective conditions. The DomB+stem product may be toxic to the cells, and the hydrophobicity of the stem may inhibit secretion.

However, a similar construct representing Gly296-Ala413 analogously inserted into pLS5 resulted in substantial amounts of secreted domain B protein. This form of domain B, designated herein DomB+T, contains the downstream T cell epitope. As stated above, the DomB proteins of the present invention include classical DomB and all or part of the amino acid sequence downstream from Gly395 to the Ala residue at position 413.

The DomB+T cDNA fragment was amplified by the PCR from pC8 plasmid DNA using oligonucleotide primers D2E1822p and D2E2175m. The primer sequences are:

D2E1822p KpnI XhoI

5'-cta gcg gta ccc tcg aga AAA GGG AGG CCG GGA TGT CAT ACT CCA TGT GC-3' (SEQ ID NO:17)

D2E2175m SalI NotI

5'-cgt gtg tcg acg cgg ccg cta tta GGC CAT TCT TTT CGC TCC-3' (SEQ ID NO:18)

The PCR product was cloned into pUC18 following KpnI and SalI digestion of the product. The DomB+T cDNA fragment was then released from pUC18-DomB+T by XhoI-SalI digestion and cloned into the XhoI site in pLS5 within the $MF\alpha_L$ and Gly395 of domain B+T. *S. cerevisiae* strain GL43 secrets approximately ten-fold more domain B than domain B+T.

EXAMPLE 6

Preparation of Antibodies to the Recombinant Domain B Protein

The Glu-Ala-DomB peptide which had been column-purified, denatured by heating in SDS, and reduced by treatment with DTT was used to immunize Swiss Webster mice following removal of the excess SDS. The mice yielded high-titre antibodies that were highly immunoreactive when used to probe Western blots displaying the same antigen or DEN-2 viral envelope protein.

EXAMPLE 7

Recombinantly Produced Glu-Ala-Domain B in ELISA Assays

The serological diagnosis for dengue infection is based on the detection of anti-dengue IgM and IgG in primary and secondary viral infection using standard Enzyme Linked Immunosorbent Assay (ELISA) techniques. Current assays are based on the ability of anti-dengue immunoglobulins to recognize semi-purified virus. Primary and secondary infections can be distinguished by the IgM:IgG ratios. (Innis et al., 1989; Kuno et al., 1991).

The recombinantly produced Glu-Ala-domain B purified as in paragraph B of Example 3 was tested as an antigen preparation in both IgM and IgG tests. In these ELISAs, the antigen was coated on plates, followed by sera positive for dengue antibodies and then detection by goat antihuman antibody.

Microtiter plates were coated overnight at 4° C. with 100 μl of a 5 μg/ml solution of domain B. After blocking with 3% normal goat serum, primary infected dengue 2 positive serum at a 1:100 dilution was added per well. The bound IgM was detected by the addition of goat anti-human IgM (Fc) conjugated to horseradish peroxidase. Under these conditions, the recombinant Glu-Ala-domain B did not provide positive results.

For IgG, high titer secondary dengue 2 infected sera were supplied at a 1:270 dilution and detected with goat anti-human IgG (Fc) conjugated to horseradish peroxidase. Two of the five sera gave positive reactions in this assay.

The recombinant Glu-Ala-domain B purified by the improved procedure of Example 3 is not recognized by murine polyclonal hyperimmune ascitic fluid (HMAF) to other dengue serotypes and to other flaviviruses, when assayed using a similar ELISA format. Flavivirus infected murine sera tested include, Japanese Encephalitis virus, Tick-Borne Encephalitis virus, Yellow Fever virus, Saint Louis Encephalitis virus, West Nile virus, three viral isolates of dengue serotype 1, two viral isolates of dengue serotype 3, and two viral isolates of dengue serotype 4.

Sandwich assay for the detection of any domain B-containing envelope antigen.

In an alternative enzyme immunoassay format, anti-domain B or anti-Dengue capture antibody, polyclonal or monoclonal, may be absorbed to the solid support, and sample containing an unknown quantity or serotype of dengue antigen may be added and then detected by reacting with a second anti-domain B or anti-Dengue antibody, either conjugated to a signal-generating enzyme or to be detected using a appropriate signal generating system, of which there are a multitude. This immunoassay is useful for the quantitation of recombinantly produced envelope protein or whole virus by comparing the immunoreactivity of a known concentration of domain B with that of the unknown antigen preparation. In addition, the conformational sensitivity or epitope binding site of the anti-domain B capture antibody can be varied to garner additional information regarding the conformation of dengue protein in the preparation.

To perform the sandwich enzyme immunoassay, 100 μl of anti-Dengue monoclonal antibody 9D12 or 3H5 (Henchal, E. A. et al., *Am J Trop Med Hyg* (1985) 34:162–169) was used to coat microtiter wells. The monoclonal antibodies were purified by Protein-A affinity chromatography and used at 10 μg/ml concentration (diluted in PBS: 50 mM sodium Phosphate, pH 7.0, 0.15 M NaCl). After a one hour incubation, the wells were washed three times with TBS-T (50 mM Tris-HCl PH 7.0, 0.15 M NaCl, 0.05% Tween-20), and blocked with 200 μl/well of 1% BSA in PBS for 1 hour at room temperature. Following three washes with TBS-T, 100 μl per well of a standard purified solution of domain B or an unknown sample was added to each well and captured by the bound monoclonal antibody. The domain B solution was allowed to bind the antibody for one hour at room temperature, and after three washes with TBS-T, 100 μl of Protein A affinity purified polyclonal rabbit anti-domain B serum (25 μg/Ml) diluted in PBS-T (PBS, 0.25% BSA, 0.05% Tween-20) was added to each well and allowed to bind to the bound antigen. Following three washes with TBS-T, 100 μl of alkaline phosphatase-labeled goat anti-rabbit IgG+IgM (H and L) conjugate (Caltag) diluted 1:2500 in PBS-T (previously established by titration) was added to each well. After incubation for one hour at room temperature, the plates were washed four times with TBS-T and 200 μl/well of 1 mg/ml p-nitrophenylphosphate (pNPP) substrate in alkaline phosphatase substrate buffer (25 mM Trizma base, pH 9.5, 0.15 M NaCl, 5 mM $MgCl_2$; 0.02% $NaN_2$) was added. The plates were incubated for one hour at room temperature and the absorbance of each well was measured on a Dynatech MR5000 using a sample wavelength of 410 nm and a reference wavelength of 630 nm. A typical domain B standard curve is presented in FIG. 12.

EXAMPLE 8

Immunization of Mice to Raise Neutralizing Antibodies

A. Crude DomB Immunogenicity in Mice:

Media from yeast cultures secreting DomB and a negative control yeast culture were buffer-exchanged with PBS, and total secreted proteins were concentrated for injection into mice. Six groups of five mice each (Outbred Swiss strain, Simonsen) were inoculated with the crude DomB preparation, negative control secreted protein, or saline, as listed below.

| Group | Immunogen | Adjuvant |
|---|---|---|
| I | Saline | Freund's |
| II | Saline | none |
| III | control medium | Freund's |
| IV | control medium | none |
| V | DomB medium | Freund's |
| VI | DomB medium | none |

Primary immunizations consisted of 50 μg of the immunogen diluted in phosphate buffered saline, with or without complete Freund's adjuvant as indicated above. Three boosts of 25 μg each were delivered at two-week intervals with no adjuvant (Groups II, IV, and VI) or Freund's incomplete adjuvant (Groups I, III, and V). Test bleeds were obtained one week after the first and second boosts, and the mice were bled out one week after the third boost.

Western blot and ELISA analysis of the first test bleeds confirmed a strong immune response to DomB among the Group VI (DomB, no adjuvant) mice. After the second bleed, this response was found to be titratable to greater than 1:6,400 by ELISA. Group VI was the only group that developed high titer DomB antibodies. The mice immunized with DomB in Freund's adjuvant (Group V) mounted a weak immune response; based on reactivity to the immunogen in Western blot format and DomB-ELISA antibody titers in the 100–400 range, Group V mice appeared to be immunosuppressed. The control mice (Groups I–IV) were all negative for antibody to DomB in both the Western and ELISA screens. In spite of high DomB antibody titers in Group VI mice, plaque reduction neutralization tests (PRNT) revealed that none of the mice immunized with the crude DomB produced neutralizing antibody (Table 1).

TABLE 1

Plaque Reduction Neutralization Tests of Sera from Mice Immunized with DomB in Concentrated, Total Secreted Yeast Proteins

| Group | Trial | Dilution Plaque Counts | | | | | |
|---|---|---|---|---|---|---|---|
| PBS + Freund's Adjuvants | 1 | 1:100 109, 105 | 1:200 ~100 | 1:400 ~100 | 1:4 | 1:8 | 1:16 |
| | 2 | | | | 34, 33 | 38, 30 | 44, 44 |
| PBS | 1 | 1:10 100, 106 | 1:20 ~100 | 1:40 ~100 | 1:4 | 1:8 | 1:16 |
| | 2 | | | | 29, 33 | 33, 40 | 39, 37 |
| Negative secreted proteins + Freund's | 1 | 1:10 106, 95 | 1:20 ~100 | 1:40 ~100 | 1:4 | 1:8 | 1:16 |
| | 2 | | | | 40, 35 | 37, 39 | 39, 47 |
| Negative | 1 | 1:10 | 1:20 | 1:40 | 1:4 | 1:8 | 1:16 |

TABLE 1-continued

Plaque Reduction Neutralization Tests of Sera from Mice Immunized with DomB in Concentrated, Total Secreted Yeast Proteins

| Group | Trial | Dilution Plaque Counts | | | | | |
|---|---|---|---|---|---|---|---|
| secreted proteins | 1 | 109, 94 | ~100 | ~100 | | | |
| | 2 | | | | 38, 42 | 44, 40 | 45, 42 |
| Crude DomB + Freund's | 1 | 1:10 100, 92 | 1:20 ~100 | 1:40 ~100 | 1:4 | 1:8 | 1:16 |
| | 2 | | | | 37 ± 5* | 35 ± 6* | 39 ± 3* |
| Crude DomB | 1 | 1:10 105, 91 | 1:20 ~100 | 1:40 ~100 | 1:4 | 1:8 | 1:16 |
| | 2 | | | | 39 ± 3* | 41 ± 3* | 39 ± 3* |
| DEN-2 | | 1:100 | 1:200 | 1:400 | 1:800 | 1:1600 | 1:3200 |
| HMAF | 1 | 0, 0 | 0, 0 | 0, 0 | 11, 8 | 31, 19 | 81, 75 |
| | | 1:250 | | | 1:1000 | | 1:4000 |
| | 2 | 3, 6 | | | 12, 15 | | 21, 21 |

PRNT assays performed on VERO cells (Trial 1) or BHK-21 C15 cells (Trial 2) with DEN-2 NGC strain. All plaque counts indicate the number of plaques obtained with the sera from five animals were pooled and assayed in duplicate, except those indicated (*) where each serum sample was individually assayed in duplicate and the number of plaques averaged (mean ± SD).

B. Pure DomB Immunogenicity in Mice:

In contrast to mice immunized with crude DomB, outbred ICR mice (Charles River) immunized with purified DomB demonstrated high titer DEN-2 virus neutralizing antibodies. Purified DomB, at a concentration of 3.5 mg/ml, was used to immunize mice (three per group) with 175 μg of purified DomB mixed 1:1 with Freund's adjuvant, with alum, or without adjuvant (PBS). Test bleeds taken after three inoculations were assayed by PRNT (Table 2).

TABLE 2

Plaque Reduction Neutralization Tests of Sera from Mice Immunized with Purified DomB

| Group | Trial | Dilution Plaque Counts | | | | | | 80% PRNT Titer$^{-1}$ |
|---|---|---|---|---|---|---|---|---|
| Negative Ascites Fluid | 1 | 1:10 36, 40 | 1:20 35, 34 | 1:40 40, 38 | | | | |
| | 2 | 39, 38 | 47, 45 | 41, 44 | | | | |
| DEN-2 | | 1:100 | 1:200 | 1:400 | 1:800 | 1:1600 | 1:3200 | |
| HMAF | 1 | 0, 0 | 0, 0 | 1, 0 | 2, 1 | 8, 9 | 13, 14 | 1500 |
| | 2 | 0, 1 | 1, 0 | 1, 2 | 1, 1 | 7, 6 | 16, 17 | >1600 |
| DomB no adjuvant | | 1:10 | 1:20 | 1:40 | 1:80 | 1:160 | 1:320 | |
| | 1 | 36, 29 | 28, 36 | 29, 27 | 36, 30 | 40, 25 | 28, 31 | >10 |
| | 2 | 9, 17 | 20, 15 | 22, 26 | 33, 26 | 41, 36 | 42, 47 | ~10 |
| DomB alum | | 1:10 | 1:20 | 1:40 | 1:80 | 1:160 | 1:30 | |
| | 1 | 8, 6 | 10, 9 | 10, 12 | 21, 20 | 32, 26 | 30, 28 | 10 |
| | 2 | 1, 0 | 5, 4 | 8, 7 | 12, 15 | 20, 25 | 27, 35 | 40 |
| DomB Freund's | | 1:40 | 1:80 | 1:160 | 1:320 | 1:640 | 1:1200 | |
| | 1 | 0, 0 | 1, 0 | 1, 4 | 9, 2 | ND | ND | >320 |
| | 2 | 0, 0 | 3, 4 | 5, 5 | 5, 20 | 13, 9 | 23, 20 | ~640 |

PRNT assays performed on VERO cells with DEN-2 NGC strain.
ND = Not Determined.

Mice immunized with purified DomB in the absence of adjuvant lacked neutralizing antibodies. DomB administered in combination with alum elicited low titer (80T PRNT ~1:10) neutralizing antibodies, and mice receiving purified DomB in combination with Freund's adjuvants had a high PRNT titer (BOT PRNT >1:320).

Three groups of 3 mice each, 5–6 week-old outbred ICR strain (Charles River) were used. Inoculation was intramus cularly in the rump at one site using 10 μg of antigen in 0.1 ml administered solution. Three inoculations were given to each group on days 1, 20, and 43. In one group, inoculation on day 1 incorporated complete Freunds adjuvants, on day 20 incomplete Freunds adjuvant, and that at day 43, no adjuvant. In a separate group, no adjuvant was supplied and in a third group, alum was supplied with all three inoculations. The sera were withdrawn on day 57 and the sera from each group were pooled, heat-inactivated at 56° C. for 30 minutes and tested for their ability to reduce plaques formed from VERO cells.

C. DomB Protection from Virus Challenge:

Suckling mice were immunized with purified DomB in Freund's, Alum, Hunter's TiterMax (Vaxcel), or no adjuvant for protection against an intracerebral injection of DEN-2 New Guinea C (NGC) strain. DomB administered in all adjuvants conferred comparable moderate survival against dengue virus challenges although survival was statistically significant (P<0.5 G test) only for mice immunized with DomB and Hunter's TiterMax. The results are shown in FIG. 10.

D. KLH-DomB Immunogenicity in Mice:

Two series of mouse immunizations were initiated to determine the 50% effective immunizing dose ($EID_{50}$) of unconjugated and KLH-conjugated DomB. Effects of alum and Freund's adjuvants to a no-adjuvant control are compared.

DomB was conjugated to KLH via EDC (1-ethyl-3-(3-dimethylaminopropyl) carbodiimide HCl) using the carbodiimide coupling method at a 1.5:1 DomB-to-KLH mass ratio. The amount of unconjugated and conjugated DomB used for these immunizations was normalized, relative to the amount of unconjugated DomB. This normalization was based upon the specific immunoreactivity of each preparation as assayed by indirect ELISA.

Mice were immunized with the priming does of 174, 52, or 5.2 μg (total protein) of the KLH-conjugated DomB in Freund's, alum, or no adjuvant. Additional mice were immunized with 87, 26, or 2.6 μg (total protein) of unconjugated DomB in Freund's adjuvant to allow direct comparison of conjugated and unconjugated material. Boosts consisting of one-half the priming dose are being given at two-week intervals. Test bleeds are assayed for the induction of anti-DomB antibodies by ELISA and Western blot. Final bleeds are tested for induction of a neutralizing immune response by PRNT assay as well as for the production of binding antibodies by ELISA and Western blot. The results are summarized in Table 3.

The response to unconjugated DomB with Freunds adjuvants was low compared to the results in Table 2, which had shown that unconjugated DomB induced a strong virus neutralizing response in outbred ICR mice when administered with Freunds' adjuvants. This apparent difference may be grounded in testing pooled sera for the data in Table 2. Pooling sera may mask individual variability. The variability in Table 3 may be attributed to the limited epitopes in DomB and to differences in the MHC genes for the outbred Swiss mice used in Table 3.

TABLE 3

Mouse Immune Response to Unconjugated and KLH-Conjugated Purified Domain B

| mouse | antigen | adjuvant | Final Titer Western[c] | Final Titer ELISA[c] | Final Titer $PRNT_{10}$[c] |
|---|---|---|---|---|---|
| 1 | saline | none | N/T[a] | <1:100 | N/T |
| 2 | | | N/T | <1:100 | <1:10 |
| 3 | | | N/T | <1:100 | <1:10 |
| 4 | 87 μg B | none | N/T | <1:100 | <1:10 |
| 5 | | | N/T | <1:100 | N/T |
| 6 | | | N/T | <1:100 | <1:10 |
| 7 | 87 μg B | Freund's | >1:100,000 Dblt[b] | >1:102,400 | 1:40 |
| 8 | | | N/T | <1:100 | <1:10 |
| 9 | | | 1:1,000,000 Dblt | >1:409,600 | <1:10 |
| 10 | | | N/T | <1:100 | <1:10 |
| 11 | | | 1:100,000 Dblt | 1:25,600 | <1:10 |
| 12 | 26 μg B | Freund's | N/T | <100 | <1:10 |
| 13 | | | 1:100,000 Dblt | 1:102,400 | <1:10 |
| 14 | | | 1:10,000 Dblt | 1:102,400 | N/T |
| 15 | | | 1:10,000 Dblt | >1:25,600 | <1:20[e] |
| 16 | | | 1:10,000 Dblt | 1:409,600 | <1:10 |
| 17 | 2.6 μg B | Freund's | 1:1,000 Dblt | 1:25,600 | <1:10 |
| 18 | | | N/T | <1:100 | <1:46 |
| 19 | | | N/T | <1:100 | <1:48 |
| 20 | | | N/T | <1:100 | <1:24 |
| 21 | | | N/T | <1:100 | <1:10 |
| 22 | "87 μg" | none | N/T | 1:100 | <1:10 |
| 23 | KLH-B | | <1:100 | 1:400 | <1:24 |
| 24 | | | N/T | <1:100 | <1:24 |
| 25 | | | N/T | <1:100 | <1:24 |
| 26 | | | N/T | <1:100 | <1:20 |
| 27 | "26 μg" | none | N/T | <1:100 | <1:34 |
| 28 | KLH-B | | N/T | <1:100 | <1:70 |
| 29 | | | N/T | <1:100 | <1:34 |
| 30 | | | N/T | <1:100 | N/T |
| 31 | | | N/T | <1:100 | <1:10 |
| 32 | "2.6 μg" | none | N/T | <1:100 | N/T |
| 33 | KLH-B | | N/T | <1:100 | <1:10 |
| 34 | | | N/T | <1:100 | <1:10 |

TABLE 3-continued

Mouse Immune Response to Unconjugated and KLH-Conjugated Purified Domain B

| mouse | antigen | adjuvant | Final Titer Western[c] | Final Titer ELISA[c] | Final Titer $PRNT_{10}$[c] |
|---|---|---|---|---|---|
| 35 | | | N/T | <1:100 | <1:10 |
| 36 | | | N/T | <1:100 | <1:10 |
| 37 | "87 μg" | Freund's | N/T | >1:1,600 | 1:20 |
| 38 | KLH-B | | N/T | <1:100 | <1:10 |
| 39 | | | N/T | <1:100 | <1:10 |
| 40 | | | 1:1,000 | >1:1,600 | 1:20 |
| 41 | | | N/T | <1:100 | 1:10 |
| 42 | "26 μg" | Freund's | 1:10,000 Dblt | >1:25,600 | 1:10 |
| 43 | KLH-B | | 1:10,000 Dblt | >1:25,600 | 1:2560 |
| 44 | | | 1:10,000 Dblt | >1:25,600 | 1:5120 |
| 45 | | | N/T | <1:100 | <1:10 |
| 46 | | | N/T | 1:100 | <1:10 |
| 47 | "2.6 μg" | Freund's | N/T | <1:100 | <1:10 |
| 48 | KLH-B | | N/T | <1:100 | <1:10 |
| 49 | | | <1:50 | 1:6,400 | <1:10 |
| 50 | | | N/T | <1:100 | <1:10 |
| 51 | | | <1:50 | 1:25.600 | <1:10 |
| 52 | "87 μg" | Alum | <1:100 | >1:400 | 1:60 |
| 53 | KLH-B | | N/T | <1:100 | <1:10 |
| 54 | | | <1:100 | >1:1,600 | 1:320 |
| 55 | | | <1:100 | >1:1,600 | 1:80 |
| 56 | | | 1:1000 | <1:6,400 | 1:640 |
| 62 | "26 μg" | Alum | <1:100 | 1:1,600 | 1:120 |
| 63 | KLH-B | | 1:1000 | >1:1,600 | 1:120 |
| 64 | | | N/T | <1:100 | <1:10 |
| 65 | | | 1:100 | >1:1,600 | 1:80 |
| 66 | | | N/T | <1:100 | <1:10 |
| 57 | "2.6 μg" | Alum | N/T | <1:100 | <1:10 |
| 58 | KLH-B | | N/T | >1:100 | <1:10 |
| 59 | | | N/T | <1:100 | <1:10 |
| 60 | | | N/T | <1:100 | <1:10 |
| 61 | | | N/T | <1:100 | <1:10 |

[a]N/T - not tested
[b]Dblt - a doublet at approximately 12 kD
[c]If serum was insufficient for testing at 1:10 dilution then higher initial dilutions were used and are indicated.

E. DomB Immunizations for Hybridoma Generation:

Six BALB/c mice were immunized with 87 μg of unconjugated DomB or 174 μg KLH-conjugated DomB in Freund's adjuvant. Upon demonstration of a strong anti-DomB response, the mice are sacrificed and their spleen cells fused to hybridoma cells for monoclonal antibody production.

EXAMPLE 9

Production of Domain B in Drosophila

The cloning vector p29GEB2.4PS, containing the domain B-encoding nucleotide sequence was digested with PvuII and the short fragment ligated into pMttSma, which is derived from pMttbns by digesting with BglII and inserting an adapter oligonucleotide containing an Sma site. The duplex linker adaptor inserted has the sequence PGATCCCGG. pMttsma then contains a unique SmaI site at the 3' end of sequences encoding the tPA leader. The parent vector pMttbns SmithKline contains the Drosophila metalothionein gene (mtn), the human tissue plasminogen activator secretion signal ($tPA_L$) and the SV40 early polyadenylation signal. The resulting expression vector, pMttDomB is thus obtained as shown in FIG. 11. The sequence of the fusion is shown in FIG. 9.

The resulting pMttDomB vector was transfected into Schneider S2 cells which were maintained in Schneider medium (Life Technologies, Grand Island, N.Y.) supplemented with 10% heat-inactivated FBS at 25° C. The cells were plated the day prior to transfection at $5\times10^5$ cells in 60 mm tissue culture dishes in a total volume of 4 ml Schneider medium plus 10% FBS. The Schneider cells were then cotransfected with pMttDomB and pCOHygro (a hygromycin B phosphotransferase-based selection vector obtained from SmithKline Beecham) using standard calcium phosphate transfection. 48 hours after transfection, the medium was supplemented with hygromycin at 300 μg/ml; hygromycin-resistant cells grew in 2–3 weeks. Varying levels of the cotransformed plasmids were used in the transfection procedure ranging from expression plasmid: PCOHygro, 1:1 to 100:1.

Cells cotransfected at ratios of 1:1, 5:1 and 20:1 were induced with 200 μM copper sulfate and the media and cells were harvested at days 1, 4 and 7. Western blots showed secretion of domain B into the medium.

EXAMPLE 10

Production of 60% E and 80% E in Drosophila

Using the adapted expression vector of Example 9, containing the Drosophila metalothionein gene, the human tissue plasminogen activator signal and the SV-40 early polyadenylation signal, the nucleotide sequences encoding 80% E, prM 80% E, 60% E and prM 60% E are inserted and the resulting vectors used to transform Schneider cells as described in Example 9. The mature truncated forms of the envelope protein are secreted into the medium, or properly processed, and are conformationally correct with respect to the corresponding native portions of the envelope protein.

Furthermore, crude media from these transformants employed in the protocol set forth in paragraphs A and B of Example 8 produce antibodies which are neutralizing against dengue virus.

We claim:

1. An expression system for the recombinant production and secretion of a portion of an envelope (E) protein of a Flavivirus selected from the group consisting of dengue virus, Japanese encephalitis virus (JEV), tick-borne encephalitis virus (TBE) and yellow fever virus (YF), which expression system comprises Drosophila cells modified to contain a DNA molecule which comprises (a) a first nucleotide sequence encoding said portion of said E protein of the Flavivirus strain against which protection is sought, which portion is the N-terminal 80% of the protein from residue 1 to residue 395, and (b) a second nucleotide sequence which encodes a secretory leader sequence or a secretory signal sequence operably linked to said first nucleotide sequence and positioned so as to produce a fusion protein when said first and said second nucleotide sequences are expressed in a eucaryotic cell, said encoding sequences operably linked to control sequences capable of effecting expression of said encoding nucleotide sequences in eucaryotic cells.

2. The expression system of claim 1 wherein said secretory leader sequence is human tissue plasminogen activator prepropeptide secretion leader (tPA$_L$) and optionally includes the premembrane leader of the E protein.

3. A method to produce a portion of an E protein of a Flavivirus selected from the group consisting of dengue virus, Japanese encephalitis virus (JEV), tick-borne encephalitis virus (TBE) and yellow fever virus (YF), which method comprises (a) culturing the Drosophila cells of claim 1 in culture medium under conditions favorable for expression of the encoding nucleotide sequence so that the cells secrete said portion of the E protein of the Flavivirus strain against which protection is sought, which portion is the N-terminal 80% of the protein from residue 1 to residue 395 into the medium; and (b) recovering the portion of the E protein from the culture medium.

4. A method to produce a portion of an E protein of a Flavivirus selected from the group consisting of dengue virus, Japanese encephalitis virus (JEV), tick-borne encephalitis virus (TBE) and yellow fever virus (YF), which method comprises (a) culturing the Drosophila cells of claim 2 in culture medium under conditions favorable for expression of the encoding nucleotide sequence so that the cells secrete said portion of the E protein of the Flavivirus strain against which protection is sought, which portion is the N-terminal 80% of the protein from residue 1 to residue 395 into the medium; and (b) recovering the portion of the E protein from the culture medium.

5. The expression system of claim 1 wherein the N-terminal 80% of the E protein from residue 1 to residue 395 is dengue virus E protein.

6. The method of claim 3 wherein the N-terminal 80% of the E protein from residue 1 to residue 395 is dengue virus E protein.

7. The method of claim 4 wherein the N-terminal 80% of the E protein from residue 1 to residue 395 is dengue virus E protein.

8. The expression system of claim 1, wherein the Drosophila cells are Drosophila Schneider cells.

9. The expression system of claim 2, wherein the Drosophila cells are Drosophila Schneider cells.

10. The method of claim 3, wherein the Drosophila cells are Drosophila Schneider cells.

11. The method of claim 4, wherein the Drosophila cells are Drosophila Schneider cells.

12. The expression system of claim 5, wherein the Drosophila cells are Drosophila Schneider cells.

13. The method of claim 6, wherein the Drosophila cells are Drosophila Schneider cells.

14. The method of claim 7, wherein the Drosophila cells are Drosophila Schneider cells.

* * * * *

```
                         SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
         (A) LENGTH: 3381 base pairs
         (B) TYPE: nucleic acid
         (C) STRANDEDNESS: single
         (D) TOPOLOGY: linear (ii) MOLECULE TYPE: cDNA (vi) ORIGINAL SOURCE:
         (A) ORGANISM: Dengue virus
         (B) STRAIN: Serotype 2 (Den-2)

(vii) IMMEDIATE SOURCE:
         (B) CLONE: Den-2 PR159/S1

(ix) FEATURE:
         (A) NAME/KEY: misc_feature
         (B) LOCATION: group(103, 1940, 1991, 2025)
         (D) OTHER INFORMATION: /note= "Positions in the S1 strain
             representing corrections to the wild type DEN-2 PR159
             strain reported by Hahn(Citation #1)"
             /citation= ([1])

(ix) FEATURE:
         (A) NAME/KEY: misc_feature
         (B) LOCATION: 1218
         (D) OTHER INFORMATION: /note= "G is replaced by A for
             Wild-Type sequence"

(ix) FEATURE:
         (A) NAME/KEY: misc_feature
         (B) LOCATION: 1260
         (D) OTHER INFORMATION: /note= "T is replaced by G for
             Wild-Type sequence"

(ix) FEATURE:
         (A) NAME/KEY: misc_feature
         (B) LOCATION: 1762
         (D) OTHER INFORMATION: /note= "G is replaced by A for
             Wild-Type sequence"

(ix) FEATURE:
         (A) NAME/KEY: misc_feature
         (B) LOCATION: 1929
         (D) OTHER INFORMATION: /note= "C is replaced by T for
             Wild-Type sequence"

(ix) FEATURE:
         (A) NAME/KEY: misc_feature
         (B) LOCATION: 2310
         (D) OTHER INFORMATION: /note= "A is replaced by N for
             Wild-Type sequence"

(ix) FEATURE:
         (A) NAME/KEY: misc_feature
         (B) LOCATION: 1
         (D) OTHER INFORMATION: /note= "Start of coding strand
             sequence for Capsid."

(ix) FEATURE:
         (A) NAME/KEY: misc_feature
         (B) LOCATION: 343
         (D) OTHER INFORMATION: /note= "Start of coding strand
             sequence for preMembrane"
```

-continued

```
    (ix) FEATURE:
         (A) NAME/KEY: misc_feature
         (B) LOCATION: 616
         (D) OTHER INFORMATION: /note= "Start of coding strand
             sequence for Membrane"

(ix) FEATURE:
         (A) NAME/KEY: misc_feature
         (B) LOCATION: 841
         (D) OTHER INFORMATION: /note= "Start of coding strand
             sequence for Envelope"

(ix) FEATURE:
         (A) NAME/KEY: misc_feature
         (B) LOCATION: 2326
         (D) OTHER INFORMATION: /note= "Start of coding strand
             sequence for NS1"

(x) PUBLICATION INFORMATION:
         (A) AUTHORS: Hahn, Y.S.
         (C) JOURNAL: Virology
         (D) VOLUME: 162
         (F) PAGES: 167-180
         (G) DATE: 1988

(xi) SEQUENCE DESCRIPTION: SEQ ID NO:1:

ATGAATAACC AACGGAAAAA GGCGAGAAAC ACGCCTTTCA ATATGCTGAA ACGCGAGAGA      60

AACCGCGTGT CAACTGTACA ACAGTTGACA AAGAGATTCT CACTTGGAAT GCTGCAGGGA    120

CGAGGACCAC TAAAATTGTT CATGGCCCTG GTGGCATTCC TTCGTTTCCT AACAATCCCA    180

CCAACAGCAG GATATTAAA AAGATGGGGA ACAATTAAAA AATCAAAGGC TATTAATGTT     240

CTGAGAGGCT TCAGGAAAGA GATTGGAAGG ATGCTGAATA TCTTAAACAG GAGACGTAGA    300

ACTGCAGGCA TGATCATCAT GCTGATTCCA ACAGTGATGG CGTTTCATCT GACCACACGC    360

AACGGAGAAC CACACATGAT CGTCAGTAGA CAAGAAAAAG GGAAAAGCCT TCTGTTTAAG    420

ACAAAGGACG GCACGAACAT GTGTACCCTC ATGGCCATGG ACCTTGGTGA GTTGTGTGAA    480

GACACAATCA CGTATAAATG TCCCTTTCTC AAGCAGAACG AACCAGAAGA CATAGATTGT    540

TGGTGCAACT CCACGTCCAC ATGGGTAACT TATGGGACAT GTACCACCAC AGGAGAGCAC    600

AGAAGAGAAA AAAGATCAGT GGCGCTTGTT CCACACGTGG GAATGGGATT GGAGACACGA    660

ACTGAAACAT GGATGTCATC AGAAGGGGCC TGGAAACATG CCCAGAGAAT TGAAACTTGG    720

ATTCTGAGAC ATCCAGGCTT TACCATAATG GCCGCAATCC TGGCATACAC CATAGGAACG    780

ACGCATTTCC AAAGAGTCCT GATATTCATC CTACTGACAG CCATCGCTCC TTCAATGACA    840

ATGCGCTGCA TAGGAATATC AAATAGGGAC TTTGTGGAAG GAGTGTCAGG AGGGAGTTGG    900

GTTGACATAG TTTTAGAACA TGGAAGTTGT GTGACGACGA TGGCAAAAAA TAAACCAACA    960

CTGGACTTTG AACTGATAAA AACAGAAGCC AAACAACCCG CCACCTTAAG GAAGTACTGT   1020

ATAGAGGCTA AACTGACCAA CACGACAACA GACTCGCGCT GCCCAACACA AGGGGAACCC   1080

ACCCTGAATG AAGAGCAGGA CAAAAGGTTT GTCTGCAAAC ATTCCATGGT AGACAGAGGA   1140

TGGGGAAATG GATGTGGATT ATTTGGAAAA GGAGGCATCG TGACCTGTGC CATGTTCACA   1200

TGCAAAAAGA ACATGGAGGG AAAAATTGTG CAGCCAGAAA ACCTGGAATA CACTGTCGTT   1260

ATAACACCTC ATTCAGGGGA AGAACATGCA GTCGGAAATG ACACAGGAAA ACATGGTAAA   1320

GAAGTCAAGA TAACACCACA GAGCTCCATC ACAGAGGCGG AACTGACAGG CTATGGCACT   1380

GTTACGATGG AGTGCTCTCC AAGAACGGGC CTCGACTTCA ATGAGATGGT GTTGCTGCAA   1440

ATGAAAGACA AGCTTGGCT GGTGCACAGA CAATGGTTCC TAGACCTACC GTTGCCATGG   1500

CTGCCCGGAG CAGACACACA AGGATCAAAT TGGATACAGA AAGAGACACT GGTCACCTTC   1560
```

-continued

```
AAAAATCCCC ATGCGAAAAA ACAGGATGTT GTTGTCTTAG GATCCAAGA GGGGGCCATG    1620

CATACAGCAC TCACAGGGGC TACGGAAATC CAGATGTCAT CAGGAAACCT GCTGTTCACA    1680

GGACATCTTA AGTGCAGGCT GAGAATGGAC AAATTACAAC TTAAAGGGAT GTCATACTCC    1740

ATGTGCACAG GAAAGTTTAA AGTTGTGAAG GAAATAGCAG AAACACAACA TGGAACAATA    1800

GTCATTAGAG TACAATATGA AGGAGACGGC TCTCCATGCA AGATCCCTTT TGAGATAATG    1860

GATCTGGAAA AAGACATGT TTTGGGCCGC CTGATCACAG TCAACCCAAT TGTAACAGAA     1920

AAGGACAGCC CAGTCAACAT AGAAGCAGAA CCTCCATTCG GAGACAGCTA CATCATCATA    1980

GGAGTGGAAC CAGGACAATT GAAGCTGGAC TGGTTCAAGA AAGGAAGTTC CATCGGCCAA    2040

ATGTTTGAGA CAACAATGAG GGGAGCGAAA AGAATGGCCA TTTTGGGCGA CACAGCCTGG    2100

GATTTTGGAT CTCTGGGAGG AGTGTTCACA TCAATAGGAA AGGCTCTCCA CCAGGTTTTT    2160

GGAGCAATCT ACGGGGCTGC TTTCAGTGGG GTCTCATGGA CTATGAAGAT CCTCATAGGA    2220

GTTATCATCA CATGGATAGG AATGAACTCA CGTAGCACAT CACTGTCTGT GTCACTGGTA    2280

TTAGTGGGAA TCGTGACACT GTACTTGGGA GTTATGGTGC AGGCCGATAG TGGTTGCGTT    2340

GTGAGCTGGA AGAACAAAGA ACTAAAATGT GGCAGTGGAA TATTCGTCAC AGATAACGTG    2400

CATACATGGA CAGAACAATA CAAGTTCCAA CCAGAATCCC CTTCAAAACT GGCTTCAGCC    2460

ATCCAGAAAG CTCATGAAGA GGGCATCTGT GGAATCCGCT CAGTAACAAG ACTGGAAAAT    2520

CTTATGTGGA AACAAATAAC ATCAGAATTG AATCATATTC TATCAGAAAA TGAAGTGAAA    2580

CTGACCATCA TGACAGGAGA CATCAAAGGA ATCATGCAGG TAGGAAAACG ATCTCTGCGG    2640

CCTCAACCCA CTGAGTTGAG GTATTCATGG AAAACATGGG GTAAAGCGAA AATGCTCTCC    2700

ACAGAACTCC ATAATCAGAC CTTCCTCATT GATGGTCCCG AAACAGCAGA ATGCCCCAAC    2760

ACAAACAGAG CTTGGAATTC ACTAGAAGTT GAGGACTACG GCTTTGGAGT ATTCACTACC    2820

AATATATGGC TAAGATTGAG AGAAAAGCAG GATGCATTTT GTGACTCAAA ACTCATGTCA    2880

GCGGCCATAA AGGACAACAG AGCCGTCCAT GCTGATATGG GTTATTGGAT AGAAAGCGCA    2940

CTCAATGATA CATGGAAGAT AGAGAAAGCT TCTTTCATTG AAGTCAAAAG TTGCCACTGG    3000

CCAAAGTCAC ACACTCTATG GAGTAATGGA GTGCTAGAAA GCGAGATGGT AATTCCAAAG    3060

AATTTCGCTG GACCAGTGTC ACAACATAAT AACAGACCAG CTATCACAC ACAAACAGCA     3120

GGACCTTGGC ATCTAGGCAA GCTTGAGATG GACTTTGATT TCTGCGAAGG GACTACAGTG    3180

GTGGTAACCG AGGACTGTGG AAACAGAGGG CCCTCTTTAA GAACAACCAC TGCCTCAGGA    3240

AAACTCATAA CGGAATGGTG TTGTCGATCT TGCACACTAC CACCACTAAG ATACAGAGGT    3300

GAGGATGGAT GCTGGTACGG GATGGAAATC AGACCATTGA AAGAGAAAGA AGAAAATCTG    3360

GTCAGTTCTC TGGTCACAGC C                                               3381
```

(2) INFORMATION FOR SEQ ID NO:2:

(i) SEQUENCE CHARACTERISTICS:
        (A) LENGTH: 3381 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Dengue virus
        (B) STRAIN: Serotype 2(DEN-2)

(vii) IMMEDIATE SOURCE:
        (B) CLONE: Den-2

-continued

```
   (ix) FEATURE:
        (A) NAME/KEY: CDS
        (B) LOCATION: 1..3381

(ix) FEATURE:
        (A) NAME/KEY: misc_feature
        (B) LOCATION: 1216..1218
        (D) OTHER INFORMATION: /note= "GAG(coding for Glu) is
            replaced by GAA(coding for Glu) for the  wild-type
            DEN-2 PR159
            strain(Citation #1)"
            /citation= ([1])

(ix) FEATURE:
        (A) NAME/KEY: misc_feature
        (B) LOCATION: 1258..1260
        (D) OTHER INFORMATION: /note= "GTG(coding for Val) is
            replaced for GTT(coding for Val) for the wild-type
            DEN-2 PR159 Strain(Citation #1)"
            /citation= ([1])

(ix) FEATURE:
        (A) NAME/KEY: misc_feature
        (B) LOCATION: 1762..1764
        (D) OTHER INFORMATION: /note= "ATT(coding for Ile) is
            replaced by GTT(coding for Val) for the wild-type
            DEN-2 PR159 strain(citation #1)"
            /citation= ([1])

(ix) FEATURE:
        (A) NAME/KEY: misc_feature
        (B) LOCATION: 1927..1929
        (D) OTHER INFORMATION: /note= "AGT(Coding for Ser) is
            replaced by AGC(coding for Ser) for the wild-type
            DEN-2 PR159 strain(citation #1)"
            /citation= ([1])

(ix) FEATURE:
        (A) NAME/KEY: misc_feature
        (B) LOCATION: 1
        (D) OTHER INFORMATION: /note= "Start of coding strand
            sequence for Capsid"

(ix) FEATURE:
        (A) NAME/KEY: misc_feature
        (B) LOCATION: 343
        (D) OTHER INFORMATION: /note= "Start of coding strand
            sequence for preMembrane"

(ix) FEATURE:
        (A) NAME/KEY: misc_feature
        (B) LOCATION: 616
        (D) OTHER INFORMATION: /note= "Start of coding strand
            sequence of Membrane"

(ix) FEATURE:
        (A) NAME/KEY: misc_feature
        (B) LOCATION: 841
        (D) OTHER INFORMATION: /note= "Start of coding strand
            sequence of Envelope"

(ix) FEATURE:
        (A) NAME/KEY: misc_feature
        (B) LOCATION: 2326
        (D) OTHER INFORMATION: /note= "Start of coding strand
            sequence for NS1"

(x) PUBLICATION INFORMATION:
        (A) AUTHORS: Hahn, Y.S.
        (C) JOURNAL: Virology
        (D) VOLUME: 162
        (F) PAGES: 167-180
        (G) DATE: 1988

(xi) SEQUENCE DESCRIPTION: SEQ ID NO:2:

ATG AAT AAC CAA CGG AAA AAG GCG AGA AAC ACG CCT TTC AAT ATG CTG      48
Met Asn Asn Gln Arg Lys Lys Ala Arg Asn Thr Pro Phe Asn Met Leu
 1               5                  10                  15
```

-continued

| | | |
|---|---|---|
| AAA CGC GAG AGA AAC CGC GTG TCA ACT GTA CAA CAG TTG ACA AAG AGA<br>Lys Arg Glu Arg Asn Arg Val Ser Thr Val Gln Gln Leu Thr Lys Arg<br>20                        25                        30 | 96 |
| TTC TCA CTT GGA ATG CTG CAG GGA CGA GGA CCA CTA AAA TTG TTC ATG<br>Phe Ser Leu Gly Met Leu Gln Gly Arg Gly Pro Leu Lys Leu Phe Met<br>35                        40                        45 | 144 |
| GCC CTG GTG GCA TTC CTT CGT TTC CTA ACA ATC CCA CCA ACA GCA GGG<br>Ala Leu Val Ala Phe Leu Arg Phe Leu Thr Ile Pro Pro Thr Ala Gly<br>50                        55                        60 | 192 |
| ATA TTA AAA AGA TGG GGA ACA ATT AAA AAA TCA AAG GCT ATT AAT GTT<br>Ile Leu Lys Arg Trp Gly Thr Ile Lys Lys Ser Lys Ala Ile Asn Val<br>65                        70                        75                        80 | 240 |
| CTG AGA GGC TTC AGG AAA GAG ATT GGA AGG ATG CTG AAT ATC TTA AAC<br>Leu Arg Gly Phe Arg Lys Glu Ile Gly Arg Met Leu Asn Ile Leu Asn<br>85                        90                        95 | 288 |
| AGG AGA CGT AGA ACT GCA GGC ATG ATC ATC ATG CTG ATT CCA ACA GTG<br>Arg Arg Arg Arg Thr Ala Gly Met Ile Ile Met Leu Ile Pro Thr Val<br>100                     105                    110 | 336 |
| ATG GCG TTT CAT CTG ACC ACA CGC AAC GGA GAA CCA CAC ATG ATC GTC<br>Met Ala Phe His Leu Thr Thr Arg Asn Gly Glu Pro His Met Ile Val<br>115                     120                    125 | 384 |
| AGT AGA CAA GAA AAA GGG AAA AGC CTT CTG TTT AAG ACA AAG GAC GGC<br>Ser Arg Gln Glu Lys Gly Lys Ser Leu Leu Phe Lys Thr Lys Asp Gly<br>130                     135                    140 | 432 |
| ACG AAC ATG TGT ACC CTC ATG GCC ATG GAC CTT GGT GAG TTG TGT GAA<br>Thr Asn Met Cys Thr Leu Met Ala Met Asp Leu Gly Glu Leu Cys Glu<br>145                     150                    155                    160 | 480 |
| GAC ACA ATC ACG TAT AAA TGT CCC TTT CTC AAG CAG AAC GAA CCA GAA<br>Asp Thr Ile Thr Tyr Lys Cys Pro Phe Leu Lys Gln Asn Glu Pro Glu<br>165                     170                    175 | 528 |
| GAC ATA GAT TGT TGG TGC AAC TCC ACG TCC ACA TGG GTA ACT TAT GGG<br>Asp Ile Asp Cys Trp Cys Asn Ser Thr Ser Thr Trp Val Thr Tyr Gly<br>180                     185                    190 | 576 |
| ACA TGT ACC ACC ACA GGA GAG CAC AGA AGA GAA AAA AGA TCA GTG GCG<br>Thr Cys Thr Thr Thr Gly Glu His Arg Arg Glu Lys Arg Ser Val Ala<br>195                     200                    205 | 624 |
| CTT GTT CCA CAC GTG GGA ATG GGA TTG GAG ACA CGA ACT GAA ACA TGG<br>Leu Val Pro His Val Gly Met Gly Leu Glu Thr Arg Thr Glu Thr Trp<br>210                     215                    220 | 672 |
| ATG TCA TCA GAA GGG GCC TGG AAA CAT GCC CAG AGA ATT GAA ACT TGG<br>Met Ser Ser Glu Gly Ala Trp Lys His Ala Gln Arg Ile Glu Thr Trp<br>225                     230                    235                    240 | 720 |
| ATT CTG AGA CAT CCA GGC TTT ACC ATA ATG GCC GCA ATC CTG GCA TAC<br>Ile Leu Arg His Pro Gly Phe Thr Ile Met Ala Ala Ile Leu Ala Tyr<br>245                     250                    255 | 768 |
| ACC ATA GGA ACG ACG CAT TTC CAA AGA GTC CTG ATA TTC ATC CTA CTG<br>Thr Ile Gly Thr Thr His Phe Gln Arg Val Leu Ile Phe Ile Leu Leu<br>260                     265                    270 | 816 |
| ACA GCC ATC GCT CCT TCA ATG ACA ATG CGC TGC ATA GGA ATA TCA AAT<br>Thr Ala Ile Ala Pro Ser Met Thr Met Arg Cys Ile Gly Ile Ser Asn<br>275                     280                    285 | 864 |
| AGG GAC TTT GTG GAA GGA GTG TCA GGA GGG AGT TGG GTT GAC ATA GTT<br>Arg Asp Phe Val Glu Gly Val Ser Gly Gly Ser Trp Val Asp Ile Val<br>290                     295                    300 | 912 |
| TTA GAA CAT GGA AGT TGT GTG ACG ACG ATG GCA AAA AAT AAA CCA ACA<br>Leu Glu His Gly Ser Cys Val Thr Thr Met Ala Lys Asn Lys Pro Thr<br>305                     310                    315                    320 | 960 |
| CTG GAC TTT GAA CTG ATA AAA ACA GAA GCC AAA CAA CCC GCC ACC TTA<br>Leu Asp Phe Glu Leu Ile Lys Thr Glu Ala Lys Gln Pro Ala Thr Leu<br>325                     330                    335 | 1008 |

```
AGG AAG TAC TGT ATA GAG GCT AAA CTG ACC AAC ACG ACA ACA GAC TCG        1056
Arg Lys Tyr Cys Ile Glu Ala Lys Leu Thr Asn Thr Thr Thr Asp Ser
            340                 345                 350

CGC TGC CCA ACA CAA GGG GAA CCC ACC CTG AAT GAA GAG CAG GAC AAA        1104
Arg Cys Pro Thr Gln Gly Glu Pro Thr Leu Asn Glu Glu Gln Asp Lys
        355                 360                 365

AGG TTT GTC TGC AAA CAT TCC ATG GTA GAC AGA GGA TGG GGA AAT GGA        1152
Arg Phe Val Cys Lys His Ser Met Val Asp Arg Gly Trp Gly Asn Gly
370                 375                 380

TGT GGA TTA TTT GGA AAA GGA GGC ATC GTG ACC TGT GCC ATG TTC ACA        1200
Cys Gly Leu Phe Gly Lys Gly Gly Ile Val Thr Cys Ala Met Phe Thr
385                 390                 395                 400

TGC AAA AAG AAC ATG GAG GGA AAA ATT GTG CAG CCA GAA AAC CTG GAA        1248
Cys Lys Lys Asn Met Glu Gly Lys Ile Val Gln Pro Glu Asn Leu Glu
                405                 410                 415

TAC ACT GTC GTT ATA ACA CCT CAT TCA GGG GAA GAA CAT GCA GTC GGA        1296
Tyr Thr Val Val Ile Thr Pro His Ser Gly Glu Glu His Ala Val Gly
            420                 425                 430

AAT GAC ACA GGA AAA CAT GGT AAA GAA GTC AAG ATA ACA CCA CAG AGC        1344
Asn Asp Thr Gly Lys His Gly Lys Glu Val Lys Ile Thr Pro Gln Ser
        435                 440                 445

TCC ATC ACA GAG GCG GAA CTG ACA GGC TAT GGC ACT GTT ACG ATG GAG        1392
Ser Ile Thr Glu Ala Glu Leu Thr Gly Tyr Gly Thr Val Thr Met Glu
450                 455                 460

TGC TCT CCA AGA ACG GGC CTC GAC TTC AAT GAG ATG GTG TTG CTG CAA        1440
Cys Ser Pro Arg Thr Gly Leu Asp Phe Asn Glu Met Val Leu Leu Gln
465                 470                 475                 480

ATG AAA GAC AAA GCT TGG CTG GTG CAC AGA CAA TGG TTC CTA GAC CTA        1488
Met Lys Asp Lys Ala Trp Leu Val His Arg Gln Trp Phe Leu Asp Leu
                485                 490                 495

CCG TTG CCA TGG CTG CCC GGA GCA GAC ACA CAA GGA TCA AAT TGG ATA        1536
Pro Leu Pro Trp Leu Pro Gly Ala Asp Thr Gln Gly Ser Asn Trp Ile
            500                 505                 510

CAG AAA GAG ACA CTG GTC ACC TTC AAA AAT CCC CAT GCG AAA AAA CAG        1584
Gln Lys Glu Thr Leu Val Thr Phe Lys Asn Pro His Ala Lys Lys Gln
        515                 520                 525

GAT GTT GTT GTC TTA GGA TCC CAA GAG GGG GCC ATG CAT ACA GCA CTC        1632
Asp Val Val Val Leu Gly Ser Gln Glu Gly Ala Met His Thr Ala Leu
530                 535                 540

ACA GGG GCT ACG GAA ATC CAG ATG TCA TCA GGA AAC CTG CTG TTC ACA        1680
Thr Gly Ala Thr Glu Ile Gln Met Ser Ser Gly Asn Leu Leu Phe Thr
545                 550                 555                 560

GGA CAT CTT AAG TGC AGG CTG AGA ATG GAC AAA TTA CAA CTT AAA GGG        1728
Gly His Leu Lys Cys Arg Leu Arg Met Asp Lys Leu Gln Leu Lys Gly
                565                 570                 575

ATG TCA TAC TCC ATG TGC ACA GGA AAG TTT AAA GTT GTG AAG GAA ATA        1776
Met Ser Tyr Ser Met Cys Thr Gly Lys Phe Lys Val Val Lys Glu Ile
            580                 585                 590

GCA GAA ACA CAA CAT GGA ACA ATA GTC ATT AGA GTA CAA TAT GAA GGA        1824
Ala Glu Thr Gln His Gly Thr Ile Val Ile Arg Val Gln Tyr Glu Gly
        595                 600                 605

GAC GGC TCT CCA TGC AAG ATC CCT TTT GAG ATA ATG GAT CTG GAA AAA        1872
Asp Gly Ser Pro Cys Lys Ile Pro Phe Glu Ile Met Asp Leu Glu Lys
610                 615                 620

AGA CAT GTT TTG GGC CGC CTG ATC ACA GTC AAC CCA ATT GTA ACA GAA        1920
Arg His Val Leu Gly Arg Leu Ile Thr Val Asn Pro Ile Val Thr Glu
625                 630                 635                 640

AAG GAC AGC CCA GTC AAC ATA GAA GCA GAA CCT CCA TTC GGA GAC AGC        1968
Lys Asp Ser Pro Val Asn Ile Glu Ala Glu Pro Pro Phe Gly Asp Ser
                645                 650                 655
```

```
TAC ATC ATC ATA GGA GTG GAA CCA GGA CAA TTG AAG CTG GAC TGG TTC      2016
Tyr Ile Ile Ile Gly Val Glu Pro Gly Gln Leu Lys Leu Asp Trp Phe
            660                 665                 670

AAG AAA GGA AGT TCC ATC GGC CAA ATG TTT GAG ACA ACA ATG AGG GGA      2064
Lys Lys Gly Ser Ser Ile Gly Gln Met Phe Glu Thr Thr Met Arg Gly
675                 680                 685

GCG AAA AGA ATG GCC ATT TTG GGC GAC ACA GCC TGG GAT TTT GGA TCT      2112
Ala Lys Arg Met Ala Ile Leu Gly Asp Thr Ala Trp Asp Phe Gly Ser
        690                 695                 700

CTG GGA GGA GTG TTC ACA TCA ATA GGA AAG GCT CTC CAC CAG GTT TTT      2160
Leu Gly Gly Val Phe Thr Ser Ile Gly Lys Ala Leu His Gln Val Phe
705                 710                 715                 720

GGA GCA ATC TAC GGG GCT GCT TTC AGT GGG GTC TCA TGG ACT ATG AAG      2208
Gly Ala Ile Tyr Gly Ala Ala Phe Ser Gly Val Ser Trp Thr Met Lys
            725                 730                 735

ATC CTC ATA GGA GTT ATC ATC ACA TGG ATA GGA ATG AAC TCA CGT AGC      2256
Ile Leu Ile Gly Val Ile Ile Thr Trp Ile Gly Met Asn Ser Arg Ser
        740                 745                 750

ACA TCA CTG TCT GTG TCA CTG GTA TTA GTG GGA ATC GTG ACA CTG TAC      2304
Thr Ser Leu Ser Val Ser Leu Val Leu Val Gly Ile Val Thr Leu Tyr
    755                 760                 765

TTG GGA GTT ATG GTG CAG GCC GAT AGT GGT TGC GTT GTG AGC TGG AAG      2352
Leu Gly Val Met Val Gln Ala Asp Ser Gly Cys Val Val Ser Trp Lys
770                 775                 780

AAC AAA GAA CTA AAA TGT GGC AGT GGA ATA TTC GTC ACA GAT AAC GTG      2400
Asn Lys Glu Leu Lys Cys Gly Ser Gly Ile Phe Val Thr Asp Asn Val
785                 790                 795                 800

CAT ACA TGG ACA GAA CAA TAC AAG TTC CAA CCA GAA TCC CCT TCA AAA      2448
His Thr Trp Thr Glu Gln Tyr Lys Phe Gln Pro Glu Ser Pro Ser Lys
            805                 810                 815

CTG GCT TCA GCC ATC CAG AAA GCT CAT GAA GAG GGC ATC TGT GGA ATC      2496
Leu Ala Ser Ala Ile Gln Lys Ala His Glu Glu Gly Ile Cys Gly Ile
        820                 825                 830

CGC TCA GTA ACA AGA CTG GAA AAT CTT ATG TGG AAA CAA ATA ACA TCA      2544
Arg Ser Val Thr Arg Leu Glu Asn Leu Met Trp Lys Gln Ile Thr Ser
    835                 840                 845

GAA TTG AAT CAT ATT CTA TCA GAA AAT GAA GTG AAA CTG ACC ATC ATG      2592
Glu Leu Asn His Ile Leu Ser Glu Asn Glu Val Lys Leu Thr Ile Met
850                 855                 860

ACA GGA GAC ATC AAA GGA ATC ATG CAG GTA GGA AAA CGA TCT CTG CGG      2640
Thr Gly Asp Ile Lys Gly Ile Met Gln Val Gly Lys Arg Ser Leu Arg
865                 870                 875                 880

CCT CAA CCC ACT GAG TTG AGG TAT TCA TGG AAA ACA TGG GGT AAA GCG      2688
Pro Gln Pro Thr Glu Leu Arg Tyr Ser Trp Lys Thr Trp Gly Lys Ala
            885                 890                 895

AAA ATG CTC TCC ACA GAA CTC CAT AAT CAG ACC TTC CTC ATT GAT GGT      2736
Lys Met Leu Ser Thr Glu Leu His Asn Gln Thr Phe Leu Ile Asp Gly
        900                 905                 910

CCC GAA ACA GCA GAA TGC CCC AAC ACA AAC AGA GCT TGG AAT TCA CTA      2784
Pro Glu Thr Ala Glu Cys Pro Asn Thr Asn Arg Ala Trp Asn Ser Leu
    915                 920                 925

GAA GTT GAG GAC TAC GGC TTT GGA GTA TTC ACT ACC AAT ATA TGG CTA      2832
Glu Val Glu Asp Tyr Gly Phe Gly Val Phe Thr Thr Asn Ile Trp Leu
930                 935                 940

AGA TTG AGA GAA AAG CAG GAT GCA TTT TGT GAC TCA AAA CTC ATG TCA      2880
Arg Leu Arg Glu Lys Gln Asp Ala Phe Cys Asp Ser Lys Leu Met Ser
945                 950                 955                 960

GCG GCC ATA AAG GAC AAC AGA GCC GTC CAT GCT GAT ATG GGT TAT TGG      2928
Ala Ala Ile Lys Asp Asn Arg Ala Val His Ala Asp Met Gly Tyr Trp
            965                 970                 975
```

```
ATA GAA AGC GCA CTC AAT GAT ACA TGG AAG ATA GAG AAA GCT TCT TTC         2976
Ile Glu Ser Ala Leu Asn Asp Thr Trp Lys Ile Glu Lys Ala Ser Phe
            980                 985                 990

ATT GAA GTC AAA AGT TGC CAC TGG CCA AAG TCA CAC ACT CTA TGG AGT         3024
Ile Glu Val Lys Ser Cys His Trp Pro Lys Ser His Thr Leu Trp Ser
        995                 1000                1005

AAT GGA GTG CTA GAA AGC GAG ATG GTA ATT CCA AAG AAT TTC GCT GGA         3072
Asn Gly Val Leu Glu Ser Glu Met Val Ile Pro Lys Asn Phe Ala Gly
    1010                1015                1020

CCA GTG TCA CAA CAT AAT AAC AGA CCA GGC TAT CAC ACA CAA ACA GCA         3120
Pro Val Ser Gln His Asn Asn Arg Pro Gly Tyr His Thr Gln Thr Ala
1025                1030                1035                1040

GGA CCT TGG CAT CTA GGC AAG CTT GAG ATG GAC TTT GAT TTC TGC GAA         3168
Gly Pro Trp His Leu Gly Lys Leu Glu Met Asp Phe Asp Phe Cys Glu
                1045                1050                1055

GGG ACT ACA GTG GTG GTA ACC GAG GAC TGT GGA AAC AGA GGG CCC TCT         3216
Gly Thr Thr Val Val Val Thr Glu Asp Cys Gly Asn Arg Gly Pro Ser
            1060                1065                1070

TTA AGA ACA ACC ACT GCC TCA GGA AAA CTC ATA ACG GAA TGG TGT TGT         3264
Leu Arg Thr Thr Thr Ala Ser Gly Lys Leu Ile Thr Glu Trp Cys Cys
        1075                1080                1085

CGA TCT TGC ACA CTA CCA CCA CTA AGA TAC AGA GGT GAG GAT GGA TGC         3312
Arg Ser Cys Thr Leu Pro Pro Leu Arg Tyr Arg Gly Glu Asp Gly Cys
    1090                1095                1100

TGG TAC GGG ATG GAA ATC AGA CCA TTG AAA GAG AAA GAA GAA AAT CTG         3360
Trp Tyr Gly Met Glu Ile Arg Pro Leu Lys Glu Lys Glu Glu Asn Leu
1105                1110                1115                1120

GTC AGT TCT CTG GTC ACA GCC                                             3381
Val Ser Ser Leu Val Thr Ala
                1125

(2) INFORMATION FOR SEQ ID NO:3:

(i) SEQUENCE CHARACTERISTICS:
        (A) LENGTH: 1127 amino acids
        (B) TYPE: amino acid
        (D) TOPOLOGY: linear (ii) MOLECULE TYPE: protein (xi) SEQUENCE DESCRIPTION: SEQ ID NO:3:

Met Asn Asn Gln Arg Lys Lys Ala Arg Asn Thr Pro Phe Asn Met Leu
 1                5                  10                  15

Lys Arg Glu Arg Asn Arg Val Ser Thr Val Gln Gln Leu Thr Lys Arg
                20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Ala Gly Met Ile Ile Met Leu Ile Pro Thr Val
                100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Lys Asp Gly
    130                 135                 140
```

-continued

```
Thr Asn Met Cys Thr Leu Met Ala Met Asp Leu Gly Glu Leu Cys Glu
145                 150                 155                 160

Asp Thr Ile Thr Tyr Lys Cys Pro Phe Leu Lys Gln Asn Glu Pro Glu
            165                 170                 175

Asp Ile Asp Cys Trp Cys Asn Ser Thr Ser Thr Trp Val Thr Tyr Gly
            180                 185                 190

Thr Cys Thr Thr Thr Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Val Leu Ile Phe Ile Leu Leu
            260                 265                 270

Thr Ala Ile Ala Pro Ser Met Thr Met Arg Cys Ile Gly Ile Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Asp Ser
            340                 345                 350

Arg Cys Pro Thr Gln Gly Glu Pro Thr Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Ile Val Thr Cys Ala Met Phe Thr
385                 390                 395                 400

Cys Lys Lys Asn Met Glu Gly Lys Ile Val Gln Pro Glu Asn Leu Glu
                405                 410                 415

Tyr Thr Val Val Ile Thr Pro His Ser Gly Glu Glu His Ala Val Gly
            420                 425                 430

Asn Asp Thr Gly Lys His Gly Lys Glu Val Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Lys Asp Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560
```

-continued

```
Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
            595                 600                 605

Asp Gly Ser Pro Cys Lys Ile Pro Phe Glu Ile Met Asp Leu Glu Lys
610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asp Trp Phe
                660                 665                 670

Lys Lys Gly Ser Ser Ile Gly Gln Met Phe Glu Thr Thr Met Arg Gly
            675                 680                 685

Ala Lys Arg Met Ala Ile Leu Gly Asp Thr Ala Trp Asp Phe Gly Ser
            690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Ser Leu Val Leu Val Gly Ile Val Thr Leu Tyr
            755                 760                 765

Leu Gly Val Met Val Gln Ala Asp Ser Gly Cys Val Val Ser Trp Lys
            770                 775                 780

Asn Lys Glu Leu Lys Cys Gly Ser Gly Ile Phe Val Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Gly Ile Cys Gly Ile
            820                 825                 830

Arg Ser Val Thr Arg Leu Glu Asn Leu Met Trp Lys Gln Ile Thr Ser
            835                 840                 845

Glu Leu Asn His Ile Leu Ser Glu Asn Glu Val Lys Leu Thr Ile Met
850                 855                 860

Thr Gly Asp Ile Lys Gly Ile Met Gln Val Gly Lys Arg Ser Leu Arg
865                 870                 875                 880

Pro Gln Pro Thr Glu Leu Arg Tyr Ser Trp Lys Thr Trp Gly Lys Ala
                885                 890                 895

Lys Met Leu Ser Thr Glu Leu His Asn Gln Thr Phe Leu Ile Asp Gly
            900                 905                 910

Pro Glu Thr Ala Glu Cys Pro Asn Thr Asn Arg Ala Trp Asn Ser Leu
            915                 920                 925

Glu Val Glu Asp Tyr Gly Phe Gly Val Phe Thr Thr Asn Ile Trp Leu
            930                 935                 940

Arg Leu Arg Glu Lys Gln Asp Ala Phe Cys Asp Ser Lys Leu Met Ser
945                 950                 955                 960

Ala Ala Ile Lys Asp Asn Arg Ala Val His Ala Asp Met Gly Tyr Trp
                965                 970                 975
```

```
Ile Glu Ser Ala Leu Asn Asp Thr Trp Lys Ile Glu Lys Ala Ser Phe
        980                 985                 990

Ile Glu Val Lys Ser Cys His Trp Pro Lys Ser His Thr Leu Trp Ser
        995                 1000                1005

Asn Gly Val Leu Glu Ser Glu Met Val Ile Pro Lys Asn Phe Ala Gly
        1010                1015                1020

Pro Val Ser Gln His Asn Asn Arg Pro Gly Tyr His Thr Gln Thr Ala
1025                1030                1035                1040

Gly Pro Trp His Leu Gly Lys Leu Glu Met Asp Phe Asp Phe Cys Glu
                    1045                1050                1055

Gly Thr Thr Val Val Val Thr Glu Asp Cys Gly Asn Arg Gly Pro Ser
                    1060                1065                1070

Leu Arg Thr Thr Thr Ala Ser Gly Lys Leu Ile Thr Glu Trp Cys Cys
        1075                1080                1085

Arg Ser Cys Thr Leu Pro Pro Leu Arg Tyr Arg Gly Glu Asp Gly Cys
        1090                1095                1100

Trp Tyr Gly Met Glu Ile Arg Pro Leu Lys Glu Lys Glu Glu Asn Leu
1105                1110                1115                1120

Val Ser Ser Leu Val Thr Ala
                    1125

(2) INFORMATION FOR SEQ ID NO:4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:4:

GGAGTATGAC ATCCCAGCTG TCGACTATCA TTTGTCCATT CTCAGCC                    47

(2) INFORMATION FOR SEQ ID NO:5:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..27

(ix) FEATURE:
        (A) NAME/KEY: CDS
        (B) LOCATION: 37..63

(ix) FEATURE:
        (A) NAME/KEY: misc_feature
        (B) LOCATION: 1..22
        (D) OTHER INFORMATION: /note= "Residues 1693 to 1714 of
            SEQ ID NO:1"

(ix) FEATURE:
        (A) NAME/KEY: misc_feature
        (B) LOCATION: 37..63
        (D) OTHER INFORMATION: /note= "Residues 1726 to 1848 of
            SEQ ID NO:1"

(xi) SEQUENCE DESCRIPTION: SEQ ID NO:5:

TGC AGG CTG AGA ATG GAC AAA TGA TAG TCGACAGCT GGG ATG TCA TAC         48
Cys Arg Leu Arg Met Asp Lys  *   *            Gly Met Ser Tyr
        1130                1135                       1
```

```
TCC ATG TGC ACA GGA                                              63
Ser Met Cys Thr Gly
  5
```

(2) INFORMATION FOR SEQ ID NO:6:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:6:

```
Cys Arg Leu Arg Met Asp Lys
  1               5
```

(2) INFORMATION FOR SEQ ID NO:7:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:7:

```
Gly Met Ser Tyr Ser Met Cys Thr Gly
  1               5
```

(2) INFORMATION FOR SEQ ID NO:8:

(i) SEQUENCE CHARACTERISTICS:
        (A) LENGTH: 564 base pairs
        (B) TYPE: nucleic acid
        (C) STRANDEDNESS: single
        (D) TOPOLOGY: linear (vi) ORIGINAL SOURCE:
        (A) ORGANISM: Saccharomyces cerevisiae (ix) FEATURE:
        (A) NAME/KEY: CDS
        (B) LOCATION: 1..564

(xi) SEQUENCE DESCRIPTION: SEQ ID NO:8:

```
ATGAGATTTC CTTCAATTTT TACTGCAGTT TTATTCGCAG CATCCTCCGC ATTAGCTGCT    60

CCAGTCAACA CTACAACAGA AGATGAAACG GCACAAATTC CGGCTGAAGC TGTCATCGGT   120

TACTCAGATT TAGAAGGGGA TTTCGATGTT GCTGTTTTGC CATTTTCCAA CAGCACAAAT   180

AACGGGTTAT TGTTTATAAA TACTACTATT GCCAGCATTG CTGCTAAAGA AGAAGGGGTA   240

TCTCTCGAGA AAAGGGAGGC TGGGATGTCA TACTCCATGT GCACAGGAAA GTTTAAAGTT   300

GTGAAGGAAA TAGCAGAAAC ACAACATGGA ACAATAGTCA TTAGAGTACA ATATGAAGGA   360

GACGGCTCTC CATGCAAGAT CCCTTTTGAG ATAATGGATC TGGAAAAAAG ACATGTTTTG   420

GGCCGCCTGA TCACAGTCAA TCCAATTGTA ACAGAAAAGG ACAGCCCAGT CAACATAGAA   480

GCAGAACCTC CATTCGGAGA CAGCTACATC ATCATAGGAG TGGAACCAGG ACAATTGAAG   540

CTGGACTGGT TCAAGAAAGG ATAA                                         564
```

(2) INFORMATION FOR SEQ ID NO:9:

(i) SEQUENCE CHARACTERISTICS:
        (A) LENGTH: 187 amino acids
        (B) TYPE: amino acid (C) STRANDEDNESS: single
            (D) TOPOLOGY: linear (ii) MOLECULE TYPE: peptide (ix) FEATURE:
            (A) NAME/KEY: Cleavage-site
            (B) LOCATION: (19^20)
            (D) OTHER INFORMATION: /note= "Signalase cleavage"

(ix) FEATURE:
            (A) NAME/KEY: Cleavage-site
            (B) LOCATION: (85^86)
            (D) OTHER INFORMATION: /note= "Kex2p cleavage"

(ix) FEATURE:
            (A) NAME/KEY: Peptide
            (B) LOCATION: 1..19
            (D) OTHER INFORMATION: /note= "MF-alpha secretion signal
                peptide"

(ix) FEATURE:
            (A) NAME/KEY: Peptide
            (B) LOCATION: 20..85
            (D) OTHER INFORMATION: /note= "MF-alpha propeptide"

(ix) FEATURE:
            (A) NAME/KEY: Domain
            (B) LOCATION: 86..187
            (D) OTHER INFORMATION: /note= "Domain B"

(xi) SEQUENCE DESCRIPTION: SEQ ID NO:9:

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Gly Met Ser Tyr Ser Met Cys Thr Gly
                85                  90                  95

Lys Phe Lys Val Val Lys Glu Ile Ala Glu Thr Gln His Gly Thr Ile
                100                 105                 110

Val Ile Arg Val Gln Tyr Glu Gly Asp Gly Ser Pro Cys Lys Ile Pro
            115                 120                 125

Phe Glu Ile Met Asp Leu Glu Lys Arg His Val Leu Gly Arg Leu Ile
        130                 135                 140

Thr Val Asn Pro Ile Val Thr Glu Lys Asp Ser Pro Val Asn Ile Glu
145                 150                 155                 160

Ala Glu Pro Pro Phe Gly Asp Ser Tyr Ile Ile Ile Gly Val Glu Pro
                165                 170                 175

Gly Gln Leu Lys Leu Asp Trp Phe Lys Lys Gly
                180                 185

(2) INFORMATION FOR SEQ ID NO:10:

(i) SEQUENCE CHARACTERISTICS:
            (A) LENGTH: 417 base pairs
            (B) TYPE: nucleic acid
            (C) STRANDEDNESS: double
            (D) TOPOLOGY: linear (ii) MOLECULE TYPE: DNA (genomic)

```
        (vi) ORIGINAL SOURCE:
             (A) ORGANISM: Drosophila (vii) IMMEDIATE SOURCE:
             (B) CLONE: p29GEB2.4PS (ix) FEATURE:
             (A) NAME/KEY: sig_peptide
             (B) LOCATION: 1..60
             (D) OTHER INFORMATION: /note= "1 tPA Secretion Signal"

(ix) FEATURE:
             (A) NAME/KEY: mat_peptide
             (B) LOCATION: 94..417
             (D) OTHER INFORMATION: /note= "1 RGARSP-domB"

(ix) FEATURE:
             (A) NAME/KEY: misc_feature
             (B) LOCATION: 112
             (D) OTHER INFORMATION: /note= "Beginning of Domain B
                 region"

(ix) FEATURE:
             (A) NAME/KEY: misc_feature
             (B) LOCATION: 61..93
             (D) OTHER INFORMATION: /note= "1 tPA Propeptide"

(ix) FEATURE:
             (A) NAME/KEY: CDS
             (B) LOCATION: 1..417

(xi) SEQUENCE DESCRIPTION: SEQ ID NO:10:

ATG GAT GCA ATG AAG AGA GGG CTC TGC TGT GTG CTG CTG CTG TGT GGA        48
Met Asp Ala Met Lys Arg Gly Leu Cys Cys Val Leu Leu Leu Cys Gly
-31 -30                 -25                 -20

GCA GTC TTC GTT TCG CCC AGC CAG GAA ATC CAT GCC CGA TTC AGA AGA        96
Ala Val Phe Val Ser Pro Ser Gln Glu Ile His Ala Arg Phe Arg Arg
    -15                 -10                  -5                  1

GGA GCC AGA TCC CCT GGG ATG TCA TAC TCC ATG TGC ACA GGA AAG TTT       144
Gly Ala Arg Ser Pro Gly Met Ser Tyr Ser Met Cys Thr Gly Lys Phe
                5                  10                  15

AAA ATT GTG AAG GAA ATA GCA GAA ACA CAA CAT GGA ACA ATA GTC ATT       192
Lys Ile Val Lys Glu Ile Ala Glu Thr Gln His Gly Thr Ile Val Ile
            20                  25                  30

AGA GTA CAA TAT GAA GGA GAC GGC TCT CCA TGC AAG ATC CCT TTT GAG       240
Arg Val Gln Tyr Glu Gly Asp Gly Ser Pro Cys Lys Ile Pro Phe Glu
     35                  40                  45

ATA ATG GAT CTG GAA AAA AGA CAT GTT TTG GGC CGC CTG ATC ACA GTC       288
Ile Met Asp Leu Glu Lys Arg His Val Leu Gly Arg Leu Ile Thr Val
 50                  55                  60                  65

AAC CCA ATT GTA ACA GAA AAG GAC AGT CCA GTC AAC ATA GAA GCA GAA       336
Asn Pro Ile Val Thr Glu Lys Asp Ser Pro Val Asn Ile Glu Ala Glu
             70                  75                  80

CCT CCA TTC GGA GAC AGC TAC ATC ATC ATA GGA GTG GAA CCA GGA CAA       384
Pro Pro Phe Gly Asp Ser Tyr Ile Ile Ile Gly Val Glu Pro Gly Gln
                 85                  90                  95

TTG AAG CTG GAC TGG TTC AAG AAA GGA TAA TAG                           417
Leu Lys Leu Asp Trp Phe Lys Lys Gly *   *
            100                 105

(2) INFORMATION FOR SEQ ID NO:11:

(i) SEQUENCE CHARACTERISTICS:
         (A) LENGTH: 137 amino acids
         (B) TYPE: amino acid
         (D) TOPOLOGY: linear (ii) MOLECULE TYPE: protein
```

(xi) SEQUENCE DESCRIPTION: SEQ ID NO:11:

| Met | Asp | Ala | Met | Lys | Arg | Gly | Leu | Cys | Cys | Val | Leu | Leu | Leu | Cys | Gly |
|---|---|---|---|---|---|---|---|---|---|---|---|---|---|---|---|
| -31 | -30 | | | | -25 | | | | | -20 | | | | | |

| Ala | Val | Phe | Val | Ser | Pro | Ser | Gln | Glu | Ile | His | Ala | Arg | Phe | Arg | Arg |
|---|---|---|---|---|---|---|---|---|---|---|---|---|---|---|---|
| -15 | | | | | -10 | | | | | -5 | | | | | 1 |

| Gly | Ala | Arg | Ser | Pro | Gly | Met | Ser | Tyr | Ser | Met | Cys | Thr | Gly | Lys | Phe |
|---|---|---|---|---|---|---|---|---|---|---|---|---|---|---|---|
| | | | 5 | | | | | 10 | | | | | 15 | | |

| Lys | Ile | Val | Lys | Glu | Ile | Ala | Glu | Thr | Gln | His | Gly | Thr | Ile | Val | Ile |
|---|---|---|---|---|---|---|---|---|---|---|---|---|---|---|---|
| | | | 20 | | | | | 25 | | | | | 30 | | |

| Arg | Val | Gln | Tyr | Glu | Gly | Asp | Gly | Ser | Pro | Cys | Lys | Ile | Pro | Phe | Glu |
|---|---|---|---|---|---|---|---|---|---|---|---|---|---|---|---|
| | 35 | | | | | 40 | | | | | 45 | | | | |

| Ile | Met | Asp | Leu | Glu | Lys | Arg | His | Val | Leu | Gly | Arg | Leu | Ile | Thr | Val |
|---|---|---|---|---|---|---|---|---|---|---|---|---|---|---|---|
| 50 | | | | | 55 | | | | | 60 | | | | | 65 |

| Asn | Pro | Ile | Val | Thr | Glu | Lys | Asp | Ser | Pro | Val | Asn | Ile | Glu | Ala | Glu |
|---|---|---|---|---|---|---|---|---|---|---|---|---|---|---|---|
| | | | | 70 | | | | | 75 | | | | | 80 | |

| Pro | Pro | Phe | Gly | Asp | Ser | Tyr | Ile | Ile | Ile | Gly | Val | Glu | Pro | Gly | Gln |
|---|---|---|---|---|---|---|---|---|---|---|---|---|---|---|---|
| | | | | 85 | | | | | 90 | | | | | 95 | |

| Leu | Lys | Leu | Asp | Trp | Phe | Lys | Lys | Gly |
|---|---|---|---|---|---|---|---|---|
| | | | 100 | | | | 105 | |

(2) INFORMATION FOR SEQ ID NO:12:

(i) SEQUENCE CHARACTERISTICS:
        (A) LENGTH: 417 base pairs
        (B) TYPE: nucleic acid
        (C) STRANDEDNESS: double
        (D) TOPOLOGY: linear (vi) ORIGINAL SOURCE:
        (A) ORGANISM: Drosophila (xi) SEQUENCE DESCRIPTION: SEQ ID NO:12:

| | | | | | |
|---|---|---|---|---|---|
| CTATTATCCT | TTCTTGAACC | AGTCCAGCTT | CAATTGTCCT | GGTTCCACTC | CTATGATGAT | 60 |
| GTAGCTGTCT | CCGAATGGAG | GTTCTGCTTC | TATGTTGACT | GGACTGTCCT | TTTCTGTTAC | 120 |
| AATTGGGTTG | ACTGTGATCA | GGCGGCCCAA | ACATGTCTT | TTTTCCAGAT | CCATTATCTC | 180 |
| AAAAGGGATC | TTGCATGGAG | AGCCGTCTCC | TTCATATTGT | ACTCTAATGA | CTATTGTTCC | 240 |
| ATGTTGTGTT | TCTGCTATTT | CCTTCACAAT | TTTAAACTTT | CCTGTGCACA | TGGAGTATGA | 300 |
| CATCCCAGGG | GATCTGGCTC | CTCTTCTGAA | TCGGGCATGG | ATTTCCTGGC | TGGGCGAAAC | 360 |
| GAAGACTGCT | CCACACAGCA | GCAGCACACA | GCAGAGCCCT | CTCTTCATTG | CATCCAT | 417 |

(2) INFORMATION FOR SEQ ID NO:13:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (vi) ORIGINAL SOURCE:
        (A) ORGANISM: Dengue virus (ix) FEATURE:
        (A) NAME/KEY: misc_feature
        (B) LOCATION: 27..46
        (D) OTHER INFORMATION: /note= "Residues 841 to 860 of SEQ
           ID NO:1"

(xi) SEQUENCE DESCRIPTION: SEQ ID NO:13:

CTTCTAGATC TCGAGTACCC GGGACCATGC GCTGCATAGG AATATC      46

(2) INFORMATION FOR SEQ ID NO:14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 20..35
        (D) OTHER INFORMATION: /note= "Complementary DNA to
            nucleotides 2010-2025 of SEQ ID NO:1."

(xi) SEQUENCE DESCRIPTION: SEQ ID NO:14:

GCTCTAGAGT CGACTATTAT CCTTTCTTGA ACCAG                         35

(2) INFORMATION FOR SEQ ID NO:15:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:15:

Glu Ala Gly Met Ser Tyr Ser Met Xaa Thr Gly Lys Phe Xaa Val Val
1               5                  10               15

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 20..35
        (D) OTHER INFORMATION: /note= "Complementary DNA to
            nucleotides 2160-2175 of SEQ ID NO:1."

(xi) SEQUENCE DESCRIPTION: SEQ ID NO:16:

GCTCTAGAGT CGACTATTAC CCGTAGATTG CTCCG                         35

(2) INFORMATION FOR SEQ ID NO:17:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:17:

CTAGCGGTAC CCTCGAGAAA AGGGAGGCCG GGATGTCATA CTCCATGTGC          50

(2) INFORMATION FOR SEQ ID NO:18:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 25..42
        (D) OTHER INFORMATION: /note= "Corresponding DNA to
            nucleotides 2062-2079 of SEQ ID NO:1."

-continued (xi) SEQUENCE DESCRIPTION: SEQ ID NO:18:

CGTGTGTCGA CGCGGCCGCT ATTAGGCCAT TCTTTTCGCT CC                42